(12) United States Patent
Thomas et al.

(10) Patent No.: US 10,197,549 B2
(45) Date of Patent: Feb. 5, 2019

(54) WELLBORE CEMENT SIMULATOR

(71) Applicant: SCHLUMBERGER TECHNOLOGY CORPORATION, Sugar Land, TX (US)

(72) Inventors: Jeffrey Thomas, Winchester, MA (US); John David Rowatt, Harvard, MA (US); Francois M. Auzerais, Boston, MA (US); Simone Musso, Cambridge, MA (US); Smaine Zeroug, Lexington, MA (US); Kenneth Kin-nam Liang, Cambridge, MA (US); Harald Quintus-Bosz, Westport, CT (US); Joshua P. Kinsley, Needham, MA (US); Alfred J. Costa, Pepperell, MA (US); Ching-Hua Tseng, Belmont, MA (US); Julien Prosper Marc Aknin, Lexington, MA (US); Jonathan Andrew Bannister, Victoria (AU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/301,896

(22) PCT Filed: Apr. 2, 2015

(86) PCT No.: PCT/US2015/023967
§ 371 (c)(1),
(2) Date: Oct. 4, 2016

(87) PCT Pub. No.: WO2015/153823
PCT Pub. Date: Oct. 8, 2015

(65) Prior Publication Data
US 2017/0205388 A1    Jul. 20, 2017

Related U.S. Application Data

(60) Provisional application No. 61/975,619, filed on Apr. 4, 2014.

(51) Int. Cl.
*E21B 33/13* (2006.01)
*G01N 33/38* (2006.01)
(Continued)

(52) U.S. Cl.
CPC ........... *G01N 33/383* (2013.01); *E21B 33/14* (2013.01); *E21B 41/0092* (2013.01)

(58) Field of Classification Search
CPC ........... C04B 28/02; C04B 28/04; C09K 8/46; C09K 8/42; E21B 33/13; E21B 33/14;
(Continued)

(56) References Cited

U.S. PATENT DOCUMENTS 7,240,545 B1    7/2007  Jennings
2004/0221644 A1  11/2004 Go Boncan et al.
(Continued)

FOREIGN PATENT DOCUMENTS

FR            2981453 A1    4/2013
WO      WO2014007878 A1    1/2014

OTHER PUBLICATIONS

Machine Translation of Foreign Document FR 2981453A1. (Year: 2018).*
Combined Search and Exam Report of European Patent Application No. 15774239.6 dated Oct. 30, 2017, 7 pages.

*Primary Examiner* — Zakiya W Bates

(57) ABSTRACT

Methods and apparatus for analyzing the material properties and behavior of cement as it hydrates under simulated downhole conditions. A wellbore cement simulator includes a temperature and pressure controlled innermost oil-filled container; an annulus in contact with the innermost container configured to hold a cement sample; a mesh sleeve in
(Continued)

(A-A')

contact with the annulus wherein the mesh sleeve is water permeable to permit hydration of the cement sample; a steel sleeve in contact with the mesh sleeve; an elastomeric bladder surrounding the steel sleeve; and a temperature and pressure controlled outermost oil-filled container.

30 Claims, 23 Drawing Sheets

(51) Int. Cl.
*E21B 33/14* (2006.01)
*E21B 41/00* (2006.01)

(58) Field of Classification Search
CPC . E21B 47/0005; E21B 33/138; E21B 41/0092
See application file for complete search history.

(56) References Cited

U.S. PATENT DOCUMENTS

| | | | | |
|---|---|---|---|---|
| 2006/0225523 | A1* | 10/2006 | Reddy | G01N 11/08 73/865.6 |
| 2007/0137285 | A1* | 6/2007 | Jennings | G01F 22/00 73/53.01 |
| 2009/0084189 | A1* | 4/2009 | McMechan | G01N 3/12 73/803 |
| 2011/0193564 | A1 | 8/2011 | Elmarsafawi | |
| 2014/0007695 | A1 | 1/2014 | Darbe et al. | |

* cited by examiner (A-A')

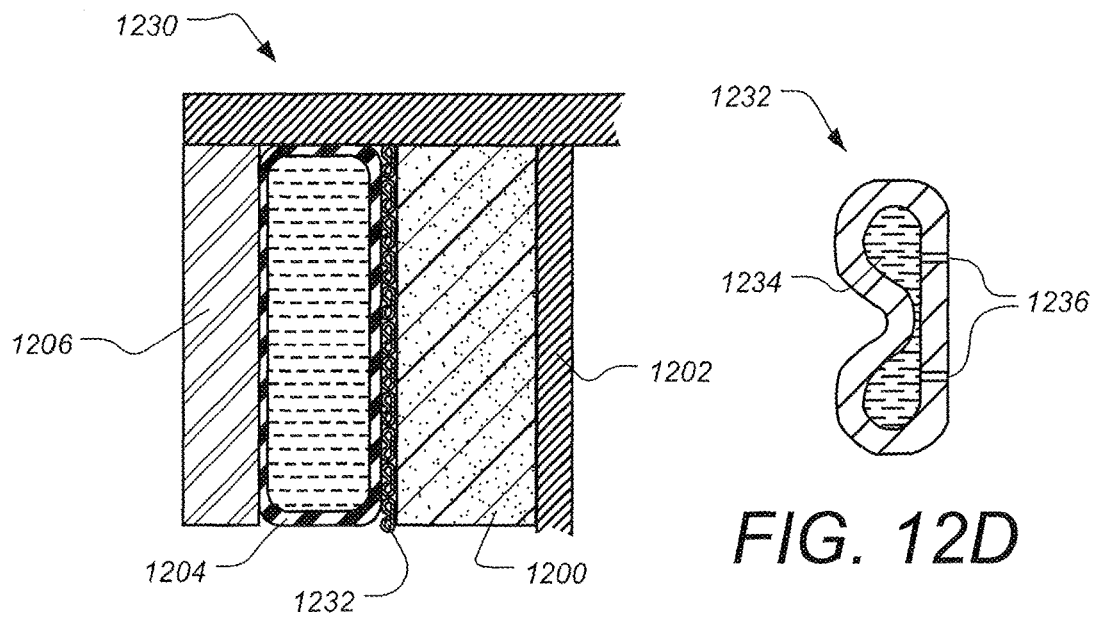
FIG. 12C
FIG. 12D
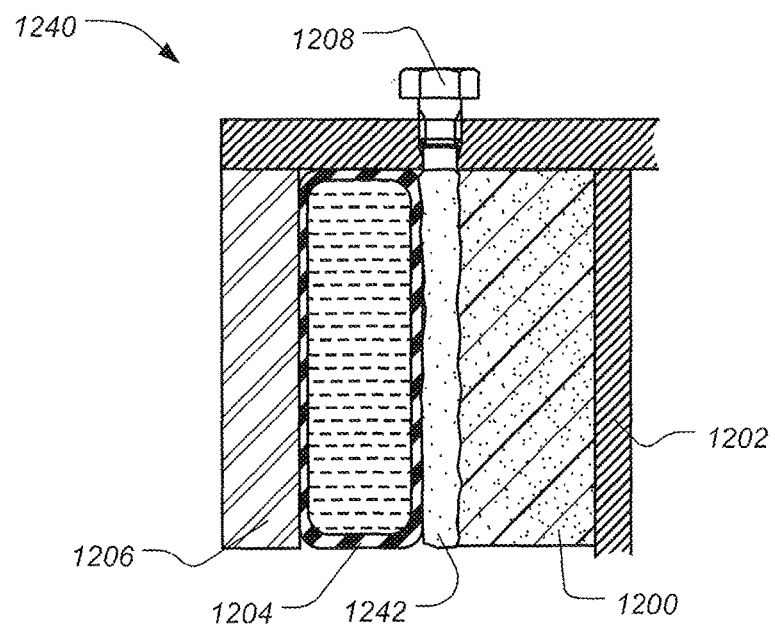
FIG. 12E

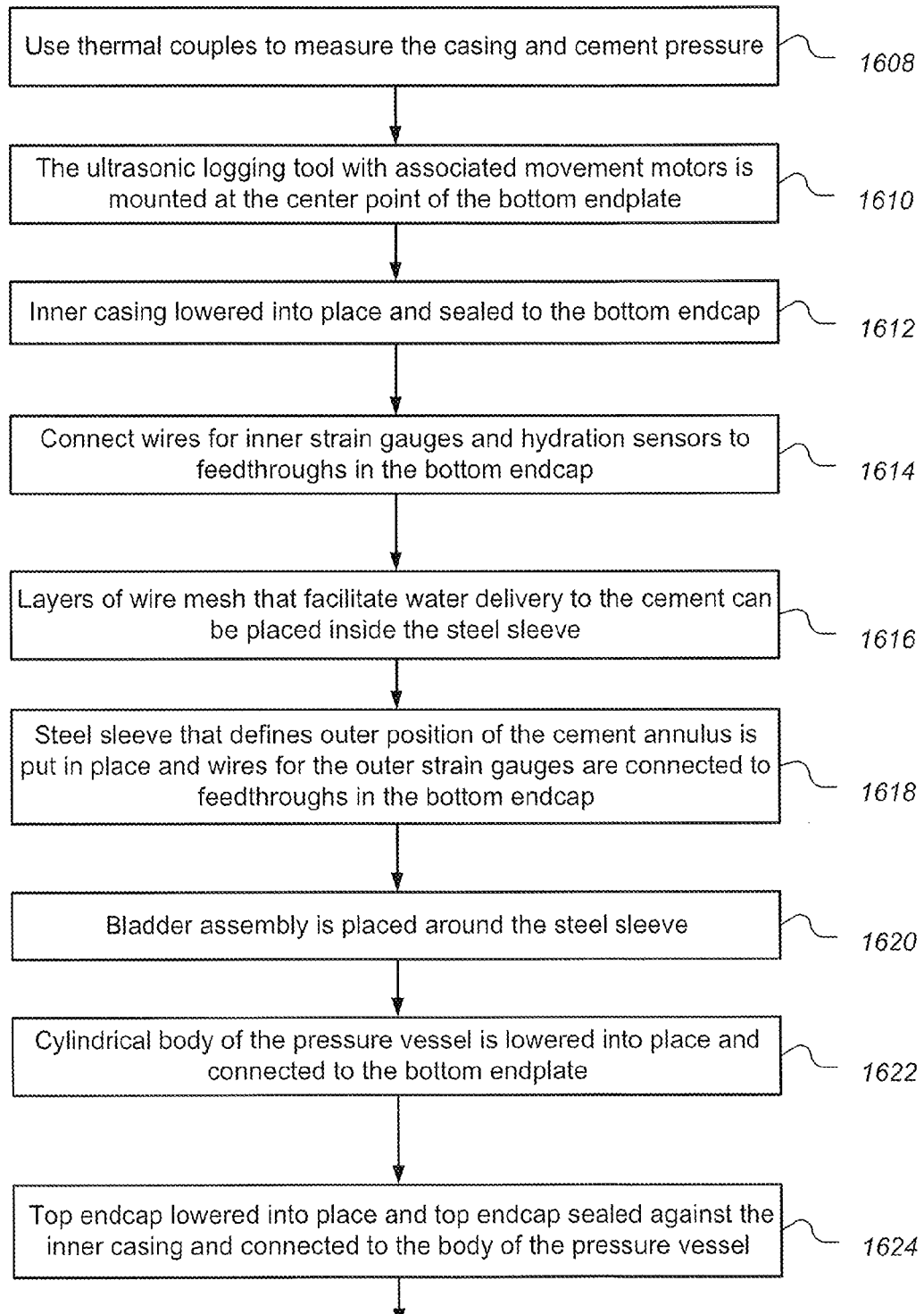
FIG. 16

WELLBORE CEMENT SIMULATOR

CROSS REFERENCE TO RELATED APPLICATIONS

This application claims priority from U.S. Ser. No. 61/975,619, filed Apr. 4, 2014, the contents of which are incorporated herein by reference.

FIELD

The subject disclosure generally relates to wellbore cementation. More particularly, the subject disclosure relates to simulation of wellbore cementation procedures.

BACKGROUND

After drilling a well, the annular space surrounding the casing is generally cemented to consolidate the well, protect the casing, and to isolate geological layers so as to prevent fluid exchange between the various formation layers. Good hydraulic isolation is thus the primary objective of cementing operations. However, problems can arise during the cementing operations, during cement hydration (including setting) or during the life of the well. For example, problems can arise with the cementing operation such as: (i) design/execution (e.g., mixing); (ii) cement placement in the wellbore (e.g., fluid channels); and (iii) loss of cement to the surrounding formation (e.g., zones without cement). Problems can also arise during cement hydration, such as: (i) liquid to solid transition (e.g., material properties); and (ii) initial stress state. Finally, problems can arise during the life of the well which may include: (i) bulk shrinkage/expansion of the cement sheath; (ii) temperature variations in the casing and/or formation; (iii) pressure variations in the casing and/or formation; and (iv) far-field stress variations (e.g., compaction, activation of shear faults).

Problems such as those outlined above can lead to the formation of fluid channels, radial cracks, disc cracks and micro-annuli in the cement which can in turn compromise well integrity. Consequently, the selection of an optimal cement formulation is important to ensure proper fluid properties for placement of the cement and material properties of the cement after it sets inside the annular region between casing and formation. This is challenging due to the wide range of environmental conditions encountered downhole, such as extremes of temperature and pressure.

Several different methods are currently used to characterize the behavior of cement formulations. These include consistometer tests to measure the thickening time of freshly-mixed slurries at different temperatures, ultrasonic cement analyzer (UCA) tests to get an empirical estimate of the compressive strength development during the first several days of curing at different temperatures and pressures, and split-ring tests to measure bulk volume changes (shrinkage or expansion) during hydration. These tests are well understood and used throughout the oilfield industry for engineering of cement formulations. Each test measures one or two specific aspects of the cement behavior, and the results of several tests are generally combined to give an overall idea of how the cement will perform.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method is described for simulating a wellbore cementation procedure of a downhole annular region between a casing and a formation wall. The method includes: placing an unset cement sample into an annular simulation volume defined in part by an inner annular surface representing an outer surface of the casing and by an outer annular surface representing an inner surface of the formation wall. The outer annular surface is configured to be radially displaceable thereby simulating radial displacement of the formation wall. The method further includes making one or more measurements during hydration of the placed cement sample; and determining one or more properties of the cement sample based on the measurements.

According to some embodiments, the outer annular surface is radially displaceable such that it simulates formation wall responses to cement pressure and cement volume changes for various formation stiffness values. According to some embodiments, the outer annular surface is at least partially supported by an oil-filled outer volume that is at least partially surrounded by a compliant member that can be hydraulically controlled to simulate formation wall responses to cement pressure and cement volume changes. Temperature of oil in the outer volume can be controlled to simulate downhole temperature conditions.

According to some embodiments, the outer annular surface can be supported using one or more techniques, such as: a fluid-filled flexible metal shell, a coiled compliant high-pressure hydraulic conduit, a set of sleeves having various stiffness, a set of discrete spherical solid objects positioned within a confined outer volume, a set of hydraulically controlled circumferentially positioned bands of material, a compliant compressible sleeve confined by a rigid outer wall and can be adjusted by applying pressure in an axial direction, or a set of slats circumferentially surrounded by a plurality of bands.

According to some embodiments, the temperature and pressure of a fluid contained in an inner chamber within the inner annular surface is controlled, and the inner annular surface can be radially displaced by controlling the fluid pressure, which can simulate pressurized mud and cement in the casing, and/or a casing pressure test conducted after cement setting.

According to some embodiments, water is delivered into the annular simulation volume during hydration of the cement thereby simulating water delivery to the cement from the formation wall. According to some embodiments, the water delivery can be facilitated by one or more structures, such as: one or more metallic mesh members circumferentially positioned on the outer annular surface, a layer of porous rock material circumferentially positioned on the outer annular surface, a layer of foam material circumferentially positioned near the outer annular surface, a coiled flattened conduit having perforations and being positioned on the outer annular surface, and two or more layers of material being textured to allow water flow and being circumferentially positioned on the outer annular surface.

According to some embodiments, the properties of the cement that are determined can include: pore pressure, hydration progress, cement temperature, cement strain, casing strain, crack formation, and micro-annulus formation. Determining pore pressure of the cement can be based on measurements such as: electrical impedance 3D tomography; ultrasound; particle sensing techniques; or fiber Bragg techniques. Determining cement strain can be based on strain gauge measurements made on an outer sleeve of material that forms the outer annular surface.

Formation of cracks and/or a micro-annulus detection can be based on ultrasound measurements such as pulse-echo and pitch-catch measurements made using a plurality of ultrasonic transducers positioned within the inner annular surface.

According to some embodiments, a wellbore is cemented by carrying out a cementation procedure that has been simulated according to described simulation techniques.

A method is described for simulating a wellbore cementation procedure of a downhole annular region between a casing and a formation wall. The method includes: placing an unset cement sample into an annular simulation volume defined at least in part by an inner annular surface representing an outer surface of the casing and by an outer annular surface representing an inner surface of the formation wall; delivering water into the annular simulation volume during hydration of the placed cement thereby simulating water delivery from the formation wall; making one or more measurements during hydration of the placed cement sample; and determining properties of the cement sample based on the measurements.

A system is described for simulating a wellbore cementation procedure of a downhole annular region between a casing and a formation wall. The system includes an annular simulation volume defined at least in part by an inner annular surface representing an outer surface of the casing, and by an outer annular surface representing an inner surface of the formation wall. The outer annular surface is radially displaceable thereby simulating radial displacement of the formation wall. The system further includes a measurement system with a plurality of sensors configured to make one or more measurements during hydration of a cement sample placed in the annular simulation volume, wherein one or more properties of the cement sample can be determined based at least in part on the one or more measurements.

According to some embodiments, the system includes: an annular simulation volume defined at least in part by an inner annular surface representing an outer surface of the casing, and by an outer annular surface representing an inner surface of the formation wall; a water delivery system configured to supply water into the annular simulation volume during hydration of a cement sample placed therein; and a measurement system including a plurality of sensors configured to make one or more measurements during hydration of the cement sample from which one or more properties of the cement sample can be determined.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIGS. 12A-12H are diagrams illustrating certain aspects of various water delivery techniques for use in wellbore cement simulators, according to some embodiments;

FIGS. 16, 17 and 18 are flow charts illustrating aspects of an example test procedure of simulating wellbore cementing against a permeable formation and then conducting a pressure test, according to some embodiments.

DETAILED DESCRIPTION

Figure 1:
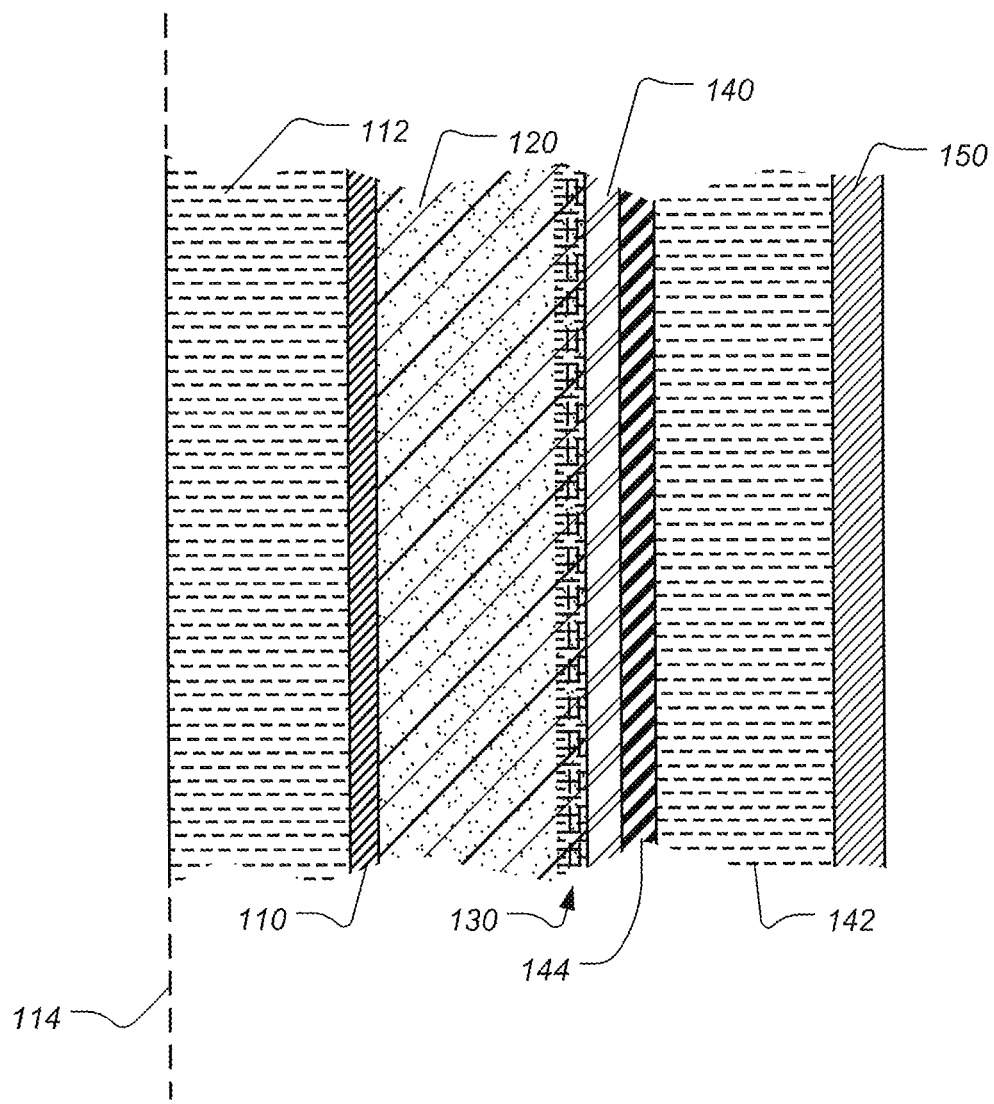
FIG. 1 is a partial cross sectional diagram illustrating certain aspects of a wellbore cement simulator, according to some embodiments.

The particulars shown herein are by way of example and for purposes of illustrative discussion of the examples of the subject disclosure only, and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

There are several limitations with known cement tests when trying to predict cement performance. These limitations include the lack of an annular geometry of the cement during the test (which strongly affects the internal stress state), the inability to simulate fluid transfer between the cement and the formation, the inability to simulate the radial movement of the formation in response to changes in the hydrostatic pressure and bulk volume of the cement, and the inability to simulate radial movement of the casing. All of these factors play a role in the ability of the cement to provide zonal isolation to the well.

According to some embodiments, a wellbore cement simulator (WCS) is described for studying the evolution of material properties and behavior of cement as it hydrates under simulated downhole conditions in realistic wellbore geometries. In some embodiments, the apparatus simulates downhole conditions including pressure, temperature, water delivery and formation and casing stiffness. In some embodiments, an array of measurements for material characterization may be obtained including detection of defect initiation and propagation, cement/casing bond quality and zonal isolation.

The WCS thus fills an important need in the industry by adapting and extending current material scale testing techniques to wellbore geometries and conditions while allowing for the development and validation of model-based evaluation techniques and measurement technologies for wellbore integrity. The WCS can also be used to evaluate the performance of downhole instruments.

Features of the WCS can be divided into two categories: 1) simulating the downhole environment, and 2) sensing (monitoring) the behavior of the cement as it hydrates and is subsequently subjected to various environmental, chemical, thermal and mechanical loads. Specific features in the simulation category include: (i) downhole temperature; (ii) wellbore and hydrostatic pressure; (iii) formation stiffness and displacement; (iv) casing stiffness and displacement; and (v) water delivery to the cement. Specific features in the sensing/monitoring category include: (i) pore pressure (formation and cement); (ii) hydration progress; (iii) cement temperature; (iv) cement strain; (v) casing strain; and (v) crack and micro-annulus formation.

Using a combination of these features allows for a full-scale annulus of cement to be hydrated at conditions that mimic the temperature, pressure, formation stiffness and water availability of a wide range of well conditions. The temperature, stress, pore pressure, hydration progress, and crack and micro-annulus formation over time can also be monitored.

According to some embodiments, a WCS includes one or more of the following functionalities: (1) controlling and measuring the pressure and temperature of the cement and formation; (2) varying the flow rate of water into the cement sheath during curing, and simulating different permeability formations ranging from tight (e.g. typical shales) to high-permeability (e.g. sandstone); (3) simulating the tendency of the formation to move radially in response to cement pressure and volume changes and to simulate a range of formation stiffness values; (4) measuring cement hydration progress, pore pressure, and temperature using fixed sensors, characterizing the cement-casing interface bonding using logging tools, and detecting cracks using passive acoustic sensors; (5) expanding or contracting the casing by varying the internal fluid pressure or other means, thus measuring the ability of the cement to resist cracking (expand casing) or debonding/microannulus formation (contract casing).

According to some embodiments, the WCS can simulate a variety of cement annulus geometries. In non-limiting examples, the apparatus can include one or more of the following: an annular geometry typical of a real wellbore; an ability to offset the casing relative to the wellbore to simulate cement placement issues related to eccentric casing; and the ability to allow for placement of multiple casing strings. According to one embodiment, the typical cement annulus dimensions are as follows: (i) annulus outer diameter of 9.625", but this may be smaller or larger to simulate other wellbore diameters; (ii) annulus inner diameter of 7.625", but this may be large or smaller to simulate other casing sizes; and a length of about 24", but this may be larger or smaller. In practice a length should be selected with an aim of minimizing end effects associated with the WCS design as well as allowing for sufficient length for sensors to be installed in the casing. According to one embodiment, the approximate casing size has an outer diameter of 7.625", but this could be larger or smaller to simulate other casing sizes; and an inner diameter that is variable to simulate various casing weights (i.e. casing wall thicknesses). When selecting the casing inner diameter, consideration should be given to allow for enough clearance for sensors to be installed in the casing. According to one embodiment, the WCS has the ability to allow cement mixing and loading into the WCS fixture in a manual or automated manner.

FIG. 1 is a partial cross sectional diagram illustrating certain aspects of a wellbore cement simulator, according to some embodiments. With respect to the centerline 114 of the device, the innermost region of the WCS 100 is defined by the casing 110. The inside of the casing 110 is filled with hydraulic oil 112. According to some embodiments, the temperature and pressure of hydraulic oil 112 can be controlled independently. In contact with the casing 110 is the cement 120 in the annulus whose inner diameter is defined by the casing 110 and whose outer diameter is defined by a combination of a mesh 130 and steel sleeve 140. The mesh 130 can be a single layer or a multi-layer element of the same or different mesh sizes. The mesh functions to allow for the distribution of water around the outer diameter of the cement annulus 120 thus simulating the delivery of water from a subterranean formation to the cement sheath. The steel sleeve 140 is slit axially at one location on its circumference and is thus allowed to expand or contract with the cement sheath. Surrounding the steel sleeve 140 is an elastomeric bladder 144 that acts as a fluid barrier between the cement annulus 120 on its inner diameter and the confining oil 142 on its outer diameter. The outer pressure vessel 150 contains the confining oil 142. According to some embodiments, the temperature and pressure of the confining oil 142 can be controlled independently.

Figure 2:
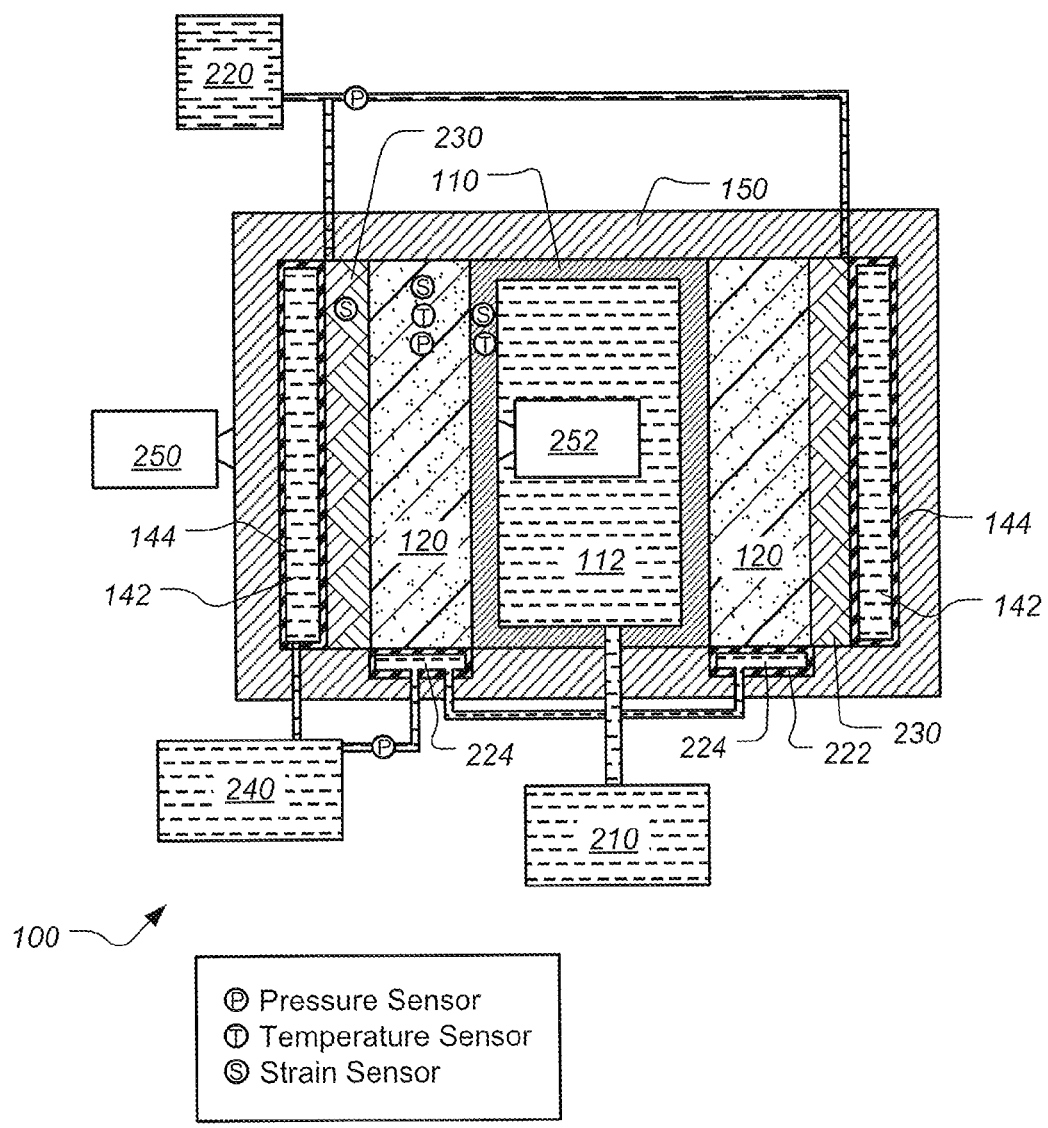
FIG. 2 is a schematic diagram showing temperature and pressure controlled hydraulics used with a wellbore cement simulator, according to some embodiments.

FIG. 2 is a schematic diagram showing temperature and pressure controlled hydraulics used with a wellbore cement simulator, according to some embodiments. The general locations for pressure, temperature and strain sensors are shown in WCS 100. In this example, a porous rock sleeve 230 is used along the outer surface of cement annulus 120, instead of the mesh layers shown in FIG. 1. Water reservoir 220 supplies water to the porous rock sleeve 230, as shown. Temperature controlled hydraulic oil supply 210 provides hydraulic oil to the inside of casing 110. Temperature controlled hydraulic oil supply 240 provides hydraulic oil 224 to pressure bladder 222, and hydraulic oil 142 to pressure bladder 144. Also shown in FIG. 2 is an ultrasonic sensing unit 252 mounted inside the casing 110. This is used for measuring the quality of the cement/casing bond as well as for detection of defects in the cement sheath itself. According to some embodiments, an x-ray source 250 is also provided outside the pressure vessel 150, although many other measurement techniques can be used, as described herein.

Figure 3:
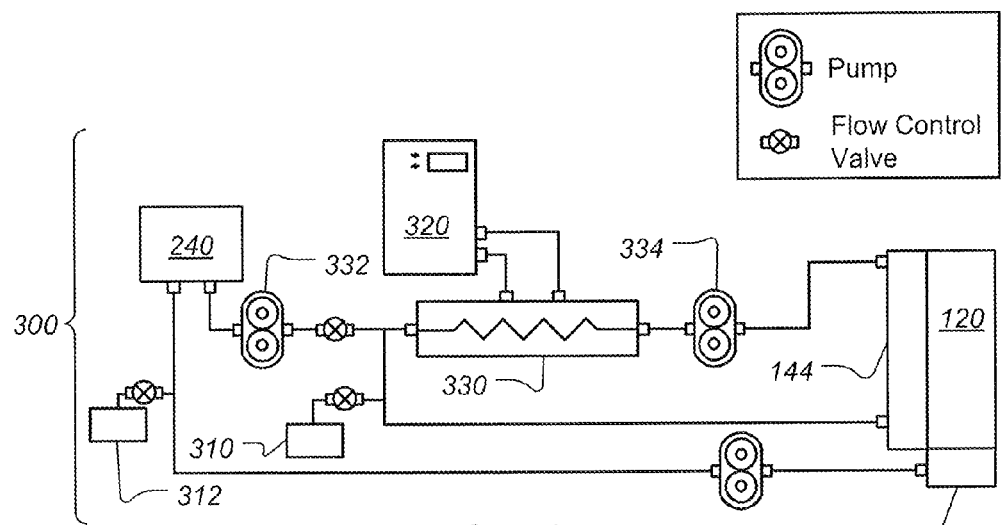
FIGS. 3, 4 and 5 are schematic diagrams illustrating further details of the hydraulic systems for the outer confining oil, the casing oil and the water delivery systems, according to some embodiments.
Figure 4:
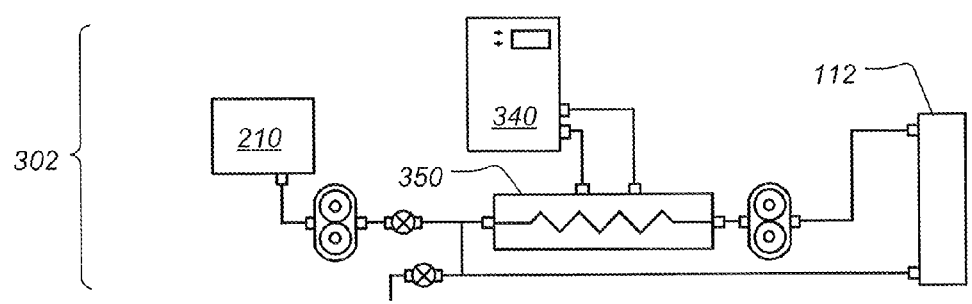
Figure 5:
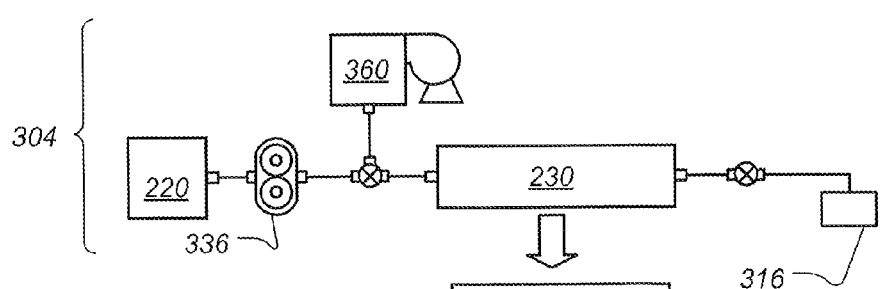

FIGS. 3, 4 and 5 are schematic diagrams illustrating further details of the hydraulic systems for the outer confining oil, the casing oil and the water delivery systems, according to some embodiments. In FIG. 3, outer confining oil system 300 provides hydraulic oil to the outside and in some cases the top and/or bottom of cement annulus 120. Oil reservoir 240, heat exchanger 330 and chiller 320 are connected to the bladders 222 and 144 using the lines, pumps and electronically controlled flow control valves as shown. Also shown are bleed tanks 310 and 312. In FIG. 4, casing oil system 302 provides hydraulic oil to the inside of the casing. Oil reservoir 210, heat exchanger 350 and chiller 340 are connected to the interior of the casing using the lines, pumps and electronically controlled flow control valves as shown. Also shown is bleed tank 314. In FIG. 5, water delivery system 304 provides water to the inside of the formation. Water supply 220 and purge air unit 360 are connected to the porous rock 230 using the lines, pump and electronically controlled flow control valve as shown. Also shown is bleed tank 316. The water delivery system 304 is controlled independently from the other hydraulic circuits, and purge air unit 360 can be used to remove air from the water before delivering it to the cement annulus through a porous media 230 to simulate a porous rock formation. In cases where mesh or other water delivery techniques are used, those structures are substituted for the porous rock 230. By providing separate reservoirs, heating, chilling, pumps and valves, for outer oil system 300, inner oil system 302 and water system 304, the temperature and pressure in each circuit can be independently controlled. The control can be manual or automated with the latter providing the ability to prescribe the temperature and pressure profiles in each circuit when coupled to a suitable controller.

Figure 6A:
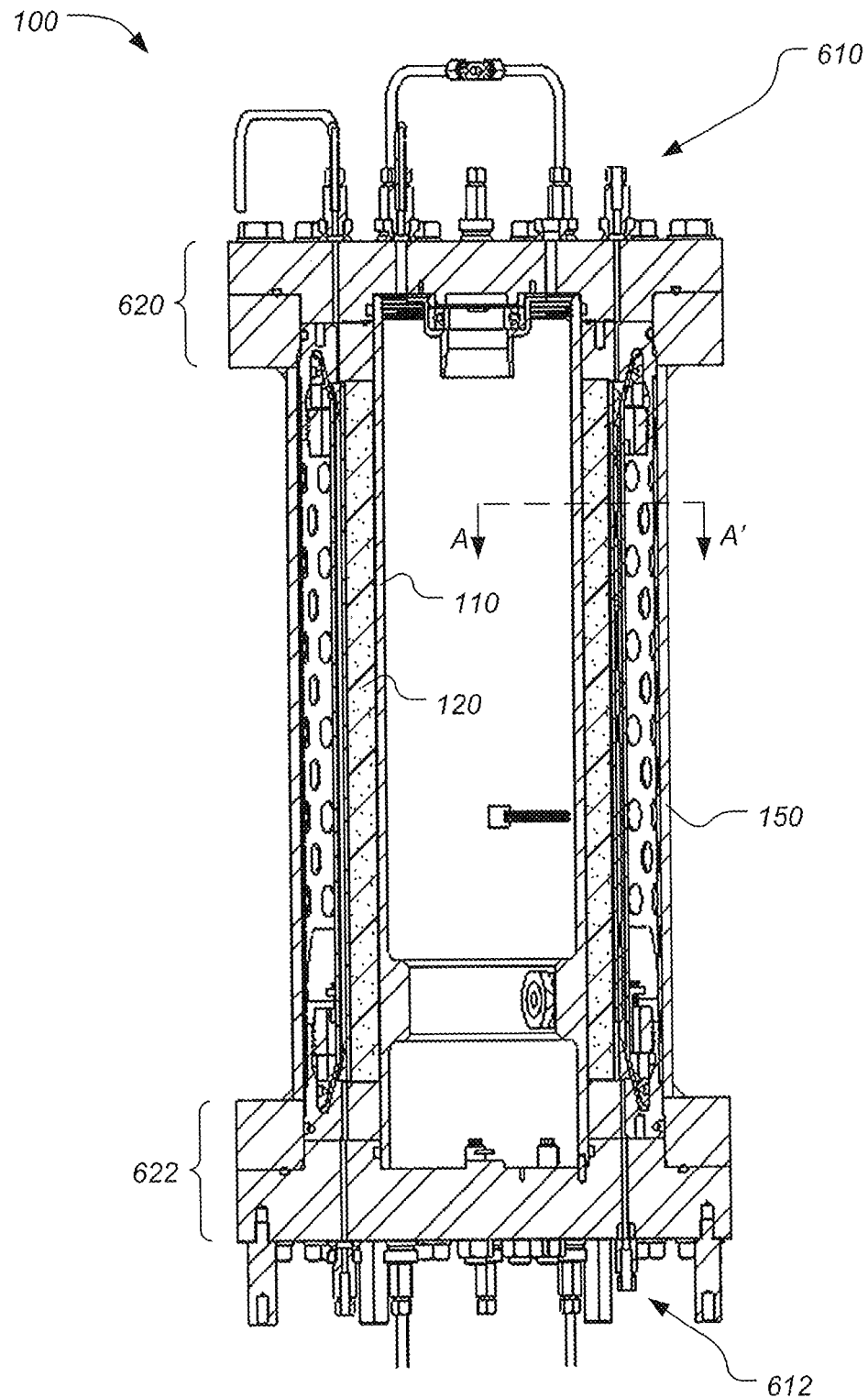
FIGS. 6A, 6B and 6C are cross-sectional diagrams illustrating certain aspects of a wellbore cement simulator, according to some embodiments.
Figure 6B:
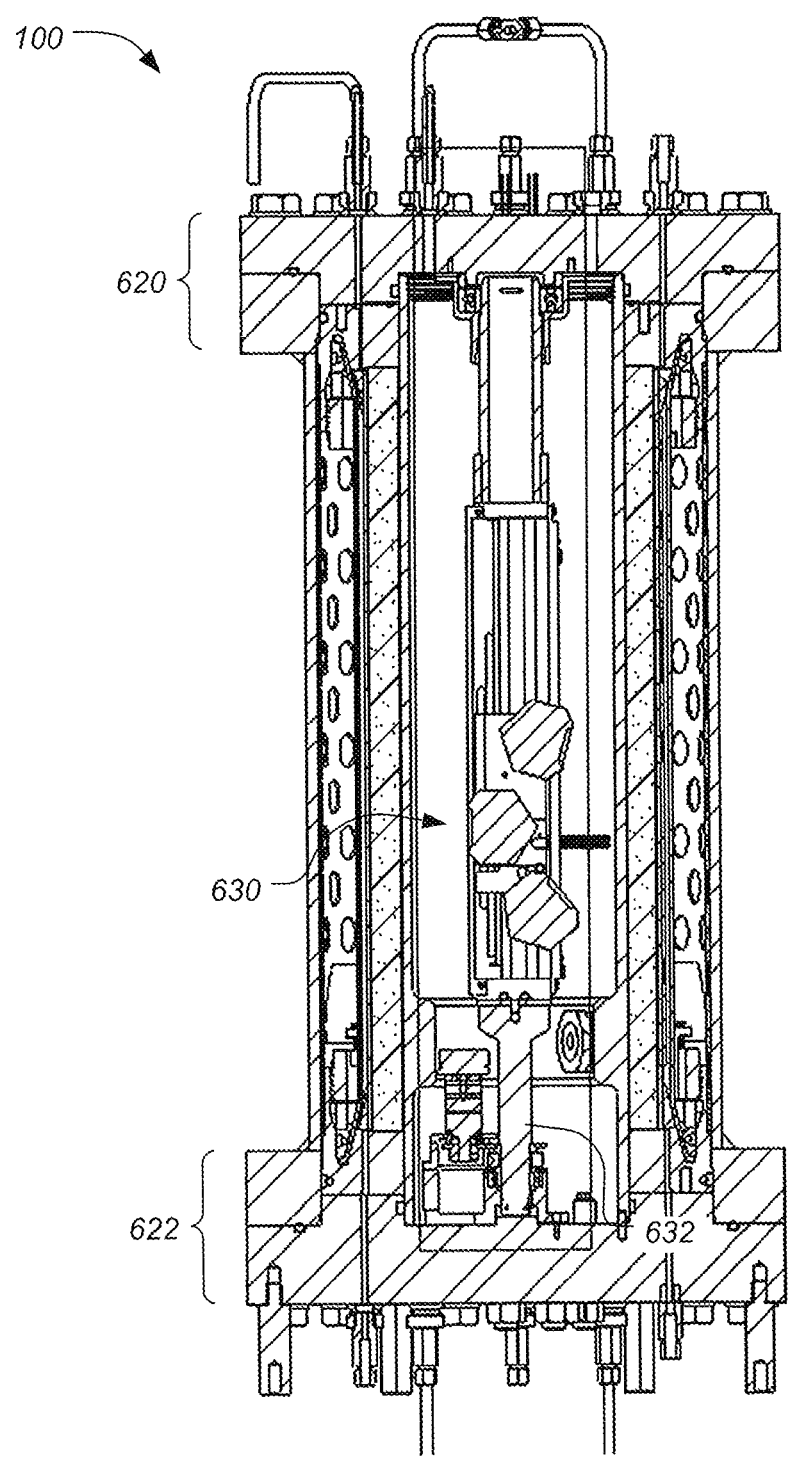
Figure 6C:
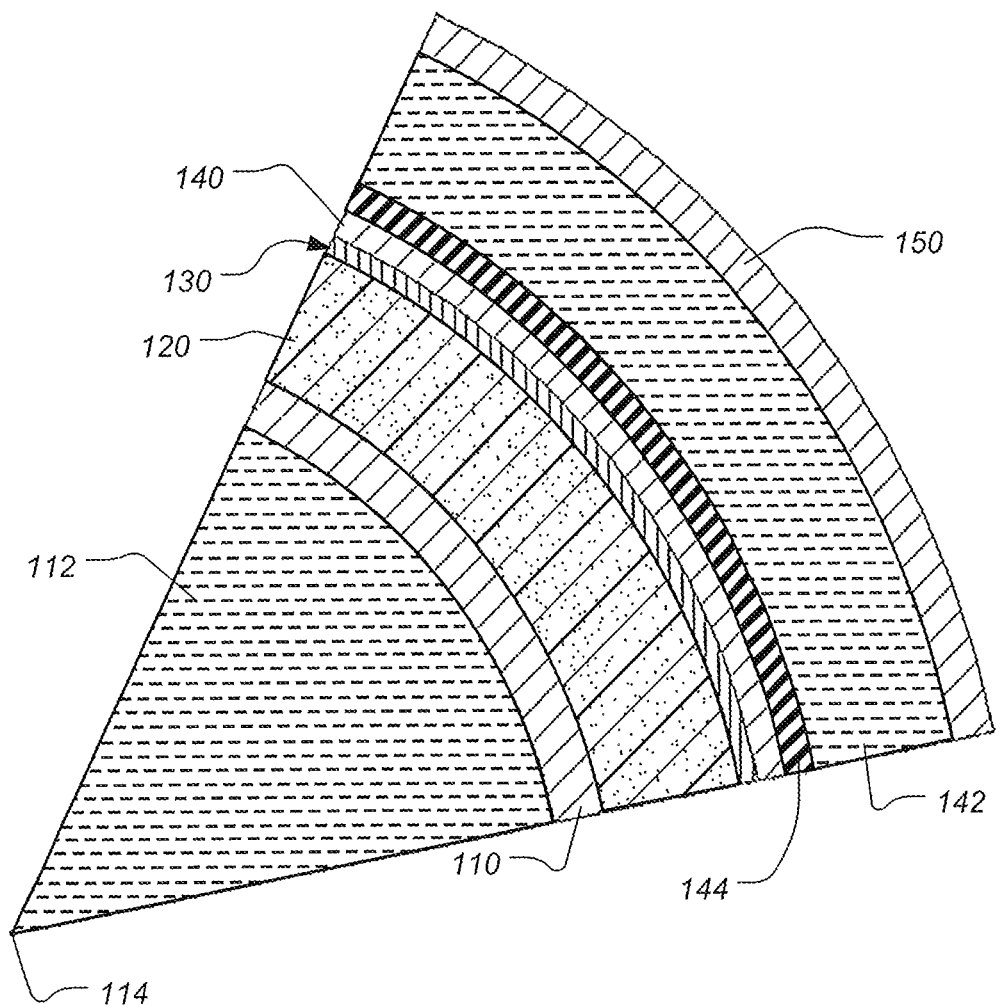

FIGS. 6A, 6B and 6C are cross-sectional diagrams illustrating certain aspects of a wellbore cement simulator, according to some embodiments. Visible in FIG. 6A are hydraulic connections 610 and 612 on the top and bottom flanges 620 and 622, respectively, of the WCS 100 through which the casing oil, cement, water and confining oil are ported to the inside of the vessel. According to some embodiments, the inner casing 100 is shown in a centralized position creating a uniform annular area for the cement 120. The confining oil 142 (shown in FIG. 1) is contained by, outer pressure vessel 150. Referring to FIG. 6B, the seals on the top and bottom flanges 620 and 622 allow a rod 632 to be passed through the center of the device 100 upon which instrumentation 630 can be mounted for monitoring the cement behavior during and after hydration. The instrumentation 630 can be manipulated via a number of means outside of the device 100. Alternatively, a measurement device can be completely enclosed in the device 100 (i.e., no penetrations through the flanges 620 and 622) and actuated via other means internal to the device 100 (e.g., internal motors). A more detailed discussion of this feature is given in the following sections infra. FIG. 6C is a partial cross-section along A-A' (shown in FIG. 6A). Visible in FIG. 6C is hydraulic oil 112 filling casing 110. Cement 120 resides in the annulus whose inner diameter is defined by casing 110 and whose outer diameter is defined by a combination of water delivery mesh 130 and steel sleeve 140. The water delivery mesh 130 can be a single layer or a multi-layer element of the same or different mesh sizes. The mesh 130 functions to allow for the distribution of water around the outer diameter of the cement 120 thus simulating the delivery of water from a subterranean formation to the cement sheath. The steel sleeve 140 is slit axially at one location on its circumference (not shown) and is thus allowed to expand or contract with the cement sheath. Surrounding the steel sleeve 140 is an elastomeric bladder 144 that acts as a fluid barrier between the cement annulus 120 on its inner diameter and the confining oil 142 on its outer diameter. The outer pressure vessel 150 contains the confining oil 142. According to some embodiments, the temperature and pressure of the confining oil 142 can be controlled independently.

Downhole Simulation Features:

According to some embodiments further detail for various features of a wellbore cement simulator for simulating downhole conditions will now be provided.

Downhole Temperature Simulation.

Temperature simulation involves both re-creating the conditions that are experienced by the cement in the well and the ability to ramp up to and back down from those conditions. With reference to FIG. 1, there are two areas that are independently controlled: (1) the volume 112 within the casing 110 (the "inner casing"); and (2) the volume 142 outside the bladder 144 (the "outer bladder"). The other surfaces of the system can be insulated, or also heated, and are generally less important to the temperature of the central area of the chamber.

According to some embodiments, the temperatures of the inner casing and the outer bladder are controlled independently. For example, see the independent hydraulic systems 300 and 302 in FIGS. 3 and 4, respectively. According to some embodiments, the heating of each volume uses direct electrical heaters. However, since pressurized oil is used in these chambers, using the oil for both pressurization and heating has been found to be both more efficient and better performing.

For temperature control, the two independent hydraulic circuits used for the inner casing and the outer bladder have approximately the same components and capabilities. For example, see the independent hydraulic systems 300 and 302 in FIGS. 3 and 4, respectively. Both the inner casing and the outer bladder regions will heat the cement mainly through conduction, so there will be a time constant associated with the thermal diffusivity of the cement. Heating and cooling the metal parts of the chamber also require power, and therefore tends to lengthen the time constant to reach steady state temperature. According to some embodiments, heat lost to the environment may be limited with insulation.

According to some embodiments, the heating and cooling is handled by a chiller/heater and heat exchanger as shown in FIGS. 3 and 4. In the heat exchangers 330 and 350, the high-pressure oil runs through a steel tube that is exposed to the heating fluid, which is at a relatively low pressure.

Simulating Wellbore and Hydrostatic Pressure.

When cement is poured into a well, it experiences the pressure of the hydraulic head of the cement slurry, while at the same time, the walls of the well bore respond to the pressure by moving outwards. Subsequently, the cement begins to hydrate and harden and develops a structure capable of holding mechanical stress, and voids capable of holding fluid pressure. According to some embodiments, the WCS system is capable of not only applying pressures and loads similar to those at depth in a wellbore, but is also able to deform and respond in a similar manner as the formation does.

Figure 7:
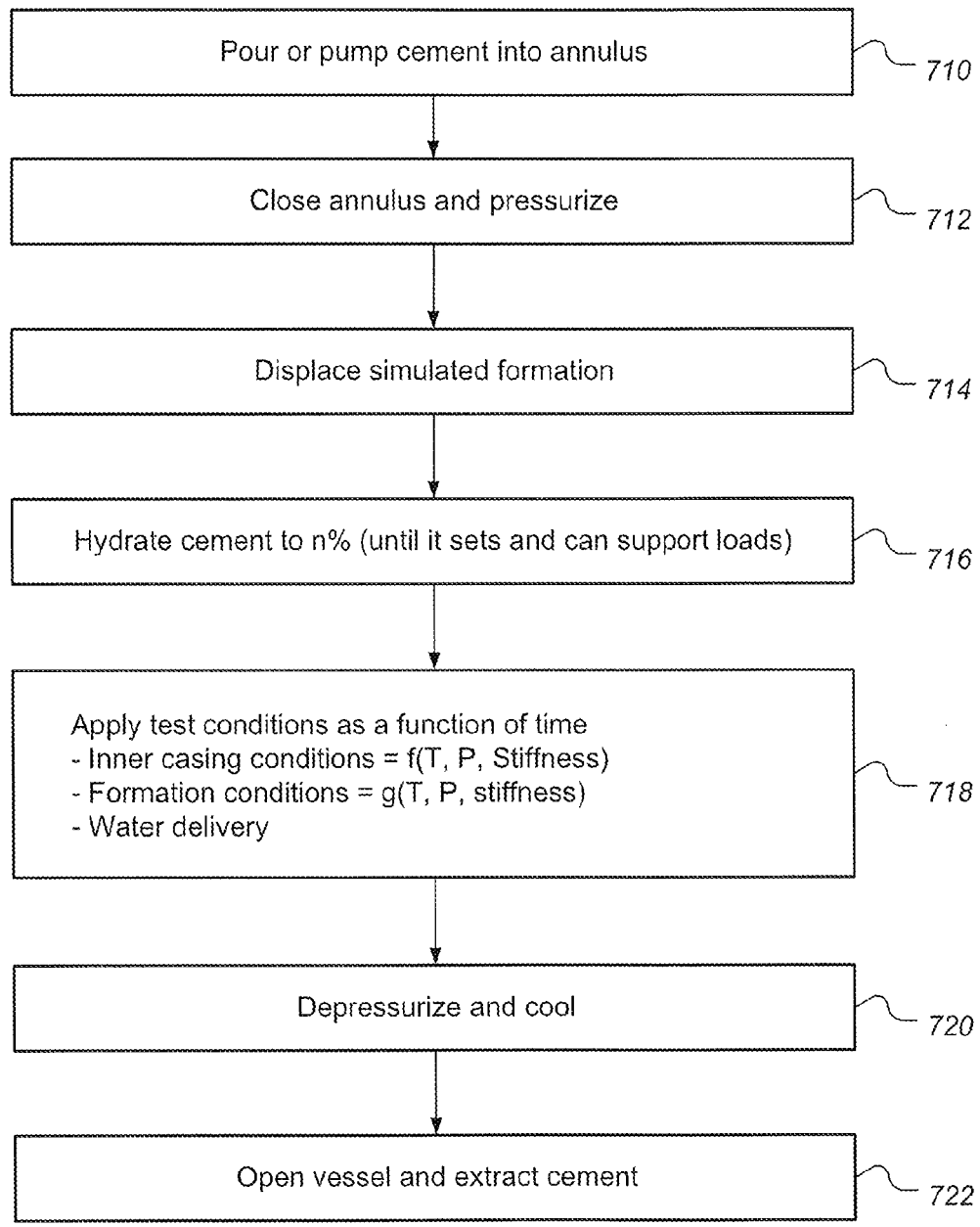
FIG. 7 is a flow chart illustrating certain aspects of a typical pressure sequence for a wellbore cement simulator, according to some embodiments.

FIG. 7 is a flow chart illustrating certain aspects of a typical pressure sequence for a wellbore cement simulator, according to some embodiments. In block 710, cement is pumped and poured into the annulus. In block 712, the annulus is sealed and pressurized. In block 714, the simulated formation surface (i.e. the outer surface of the annulus) is displaced in a way that simulates displacement of the downhole formation. In block 716 the cement is allowed to hydrate to a certain level until it can support loads. In block 718, the simulated conditions are applied as a function of time. The system uses time control of three areas of pressure: (1) the outer bladder, (2) the inner casing, and (3) the cement. When the cement hydrates, its hardness will help support some of the loads applied, so according to some embodiments, the amount of pressure applied on the cement can be experimentally determined. In order to satisfy the pressure conditions of block 718, the WCS is able to independently pressurize the outer bladder, inner casing, and cement pore fluid. In block 720 the system is depressurized and allowed to cool. In block 722 the vessel is opened and the cement is extracted. Further details of each of the pressure systems will now be provided.

Outer Bladder (Confining Oil) Pressure System.

Referring to FIG. 1, the bladder 144 mimics the rock formation by expanding and contracting the sleeve 140 that is in contact with the outside of the cement 120 according to known formation stiffness functions. As can be seen in system 300 in FIG. 3, two pumps 332 and 334 are used to control the temperature and the pressure of the outer bladder 144. The circulation pump 332 will cause the oil to go through the bladder and heat exchanger, thereby allowing temperature control. The pressurization pump 334 will pump oil into or out of the bladder, according to the size of the sleeve. The bladder 144 is simulating the stiffness of the rock, so the control of the oil flow will be dependent on understanding the volumetric change of the rock versus pressure and the volumetric change of the chamber and the oil versus pressure. The control system then applies the flow, which causes the sleeve to move a distance that mimics the response of the rock formation being simulated. Aside from modeling the stiffness of the formation, according to some embodiments, the outer bladder can also be used to model other events, such as a significant collapse of the formation, which can be modeled by letting a majority of the oil escape from bladder 144.

Inner Casing (Casing Oil) Pressure System.

The inner casing of the WCS chamber represents the casing that is used in an oil or gas well. The inside of a well casing is either filled with density-controlled mud or cement while pumping cement into a well. Due to the hydraulic head and the changes of fluid, the pressure and temperature of the fluid in the inner casing changes with time. The hydraulic system for the casing (system 302 in FIG. 4) will resemble the system used on the outer bladder system (system 300 in FIG. 3). The pressure in the inner casing is simulating the hydraulic head of the mud or cement in the bore. Pressure testing or formation fracturing will change the pressure applied to the inner casing, sometimes in an abrupt way. Both of these condition sets are considered, so the WCS system has the ability to change the pressure and temperature of the inner casing.

The cement in the annulus of the WCS, however, does not come into contact with the hydraulic oil in the inner casing. It only experiences the dimensional change and normal stresses on the contact interface between the cement and the casing. According to some embodiments, the cement is allowed to experience the correct deformation and stress conditions at the interface simply by using a casing that is similar to the actual ones used in the wellbore, and the same pressures as would be experienced at the targeted depth are applied. According to some other embodiments, the inner casing is made out of a material or in a configuration that is not similar to the actual casing. In this case, it is still possible to create the same deformation and normal stress profile by controlling the pressure inside the casing to a value that is different than the at-depth target and compensates for the differences; much like the outer bladder pressure circuit simulates rock. Such embodiments can be useful, for example, in applying a pressure bias, which would mean that the casing appears to the cement to be at a neutral condition when it is already under some pressure. This would allow the casing to shrink away from the cement when depressurization occurs at the end of a test.

Cement Pressure System.

When cement has just been placed and is still fluid, its stress state is described by a single hydrostatic pressure. However, after the cement sets it becomes effectively a two-phase material comprising a solid phase that can support mechanical stresses and an aqueous pore phase with a hydrostatic pressure that can be quite different from the mechanical stresses in the solid. As cement hydrates, the pressure of the fluid in the pores (the pore pressure) tends to decrease due to a phenomenon known as chemical shrinkage that creates a water demand inside the cement. Under some downhole conditions, pressurized fluid from the formation can flow easily into the cement to maintain the pore pressure at the initial level. In other cases, such as cementing against tight formations or between casings, the pore pressure in the cement can drop significantly, leading to bulk shrinkage of the cement.

According to some embodiments, these different downhole conditions are simulated in a WCS with an independent control system that supplies pressurized water to the cement (e.g. through a steel mesh 130 at the cement/formation interface). According to some embodiments, pressure is supplied by a volumetric pump that also measures the volume of water that enters the cement annulus over time (E.g. pump 336 in system 304 shown in FIG. 5). To simulate a highly permeable, water-filled formation, the water pressure in the mesh is kept constant throughout the run. To simulate a very tight (low-permeability) formation, or between casings, the cement is initially pressurized and then no further water is supplied. Furthermore, according to some embodiments, limiting the maximum rate at which water is supplied through the mesh to the cement simulates cementing against formations of intermediate permeability levels. In this case, the pore pressure will drop when the cement is hydrating quickly and has a high water demand that is not fully met. At later times when the cement is hydrating slowly and has a low water demand, the pore pressure will recover. Thus, the WCS can be programmed to simulate the ability of a wide variety of formations to supply water to the cement annulus.

Simulating Formation Stiffness and Displacement.

One of the suspected primary reasons for the generation of cracks and micro-annulus is the deformation of the casing and the formation under pressure. Once the cement is hydrated, it has a limited ability to respond to tensile strain without fracturing. According to some embodiments, the WCS has the ability to apply a variety of pressure combinations and resulting deformations that are typical of downhole conditions.

Figure 8A:
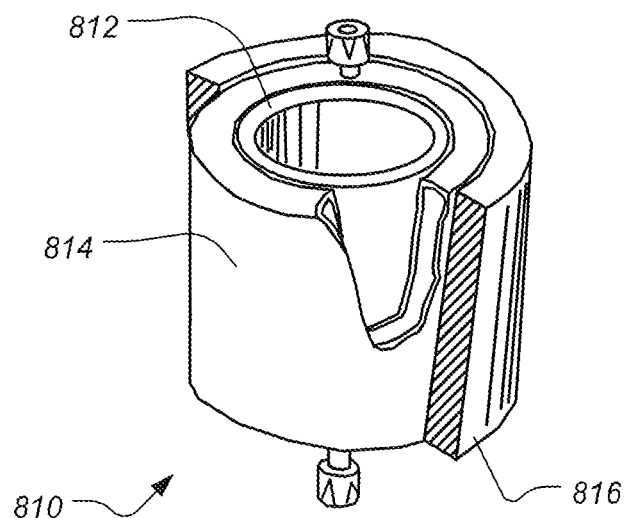
FIGS. 8A-G are diagrams illustrating various ways of providing structures for simulating formation stiffness and displacement, according to some embodiments.
Figure 8B:
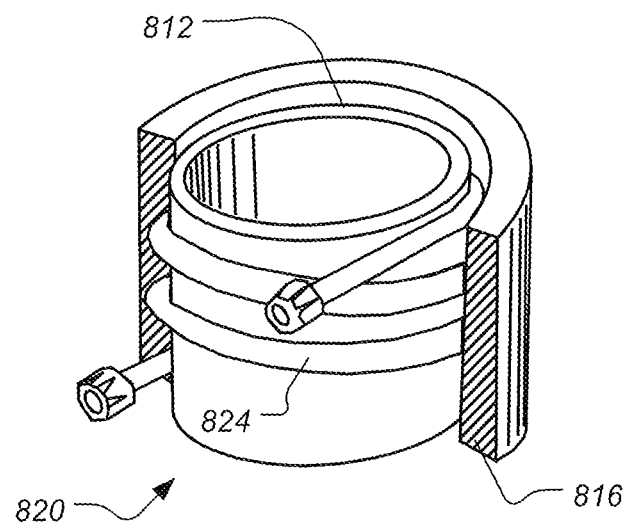
Figure 8C:
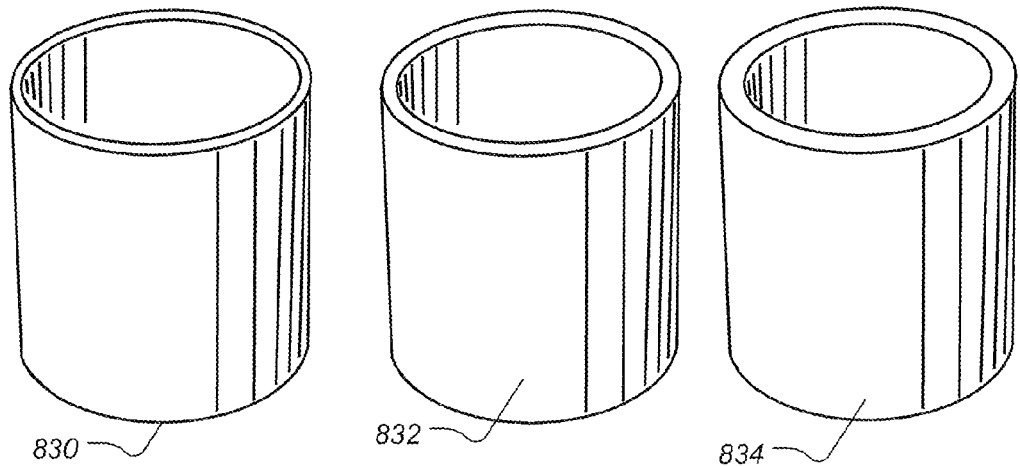
Figure 8D:
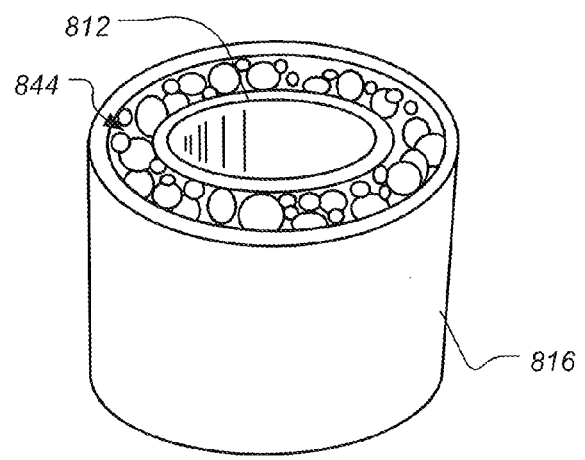

Stiffness values for formations typically encountered in wellbores can range from 5-25 GPa with resulting maximum radial deflections on the order of 1000 μm (1 mm) resulting from the hydrostatic pressure in the cement column. Thus, a significant amount of force is needed to contain the cement. As such, there are two primary means for the WCS to reasonably approximate the behavior of the formation: (1) find a backing material for the WCS that is able to mimic the stiffness and deformation of the desired formation, or (2) map the pressure to deformation characteristic of the wellbore and dynamically control the supporting structure to move the WCS wall as if it were as stiff as the desired wellbore. FIGS. 8A-G are diagrams illustrating various ways of providing structures for simulating formation stiffness and displacement, according to some embodiments. In FIG. 8A, WCS 810 has a flexible metal shell 814, made of a material such as thin titanium, as the membrane to hold high-pressure hydraulic oil. The shell is supported in the outer direction by an outer containment wall 816 and on in the inner side by a porous rock wall 812. Note that structures other than porous rock can be used according to other embodiments. In FIG. 8B, WCS 820 uses compliant high-pressure hydraulic oil line 824 between porous rock wall 812 and containment wall 816 to exert a compressive force to the porous wall 812. According to some embodiments, a series of discrete sleeves are used, examples of which are sleeves 830, 832 and 834 in FIG. 8C. Each sleeve is made of a material and has a thickness selected to approximate the stiffness and displacement characteristics of each different type of formation that is being simulated. In FIG. 8D, WCS 840 uses a set of spheres 844 to support the inner porous wall 812. The spheres 844 may be the same size, or they may be of a variety of sizes, depending on what fills the space more effectively. Softer spheres can be used for simulating rock formations having more flexibility, while stiffer spheres can be used for simulating rock formations having less flexibility. According to some embodiments, a bed of particles is provided that changes its ability to flow depending on pressure.

Figure 8E:
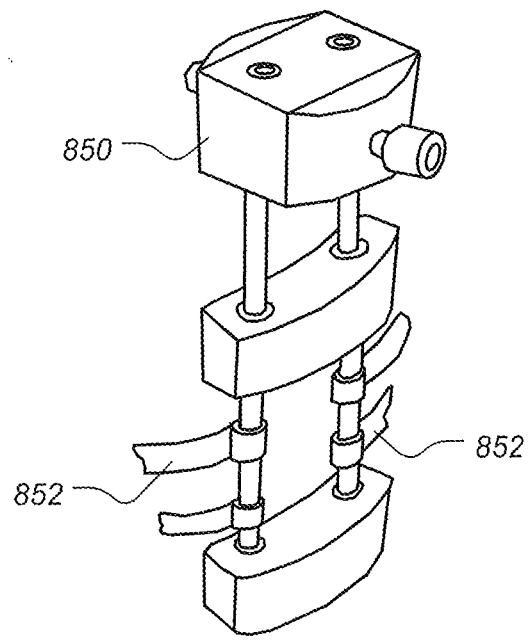
Figure 8F:
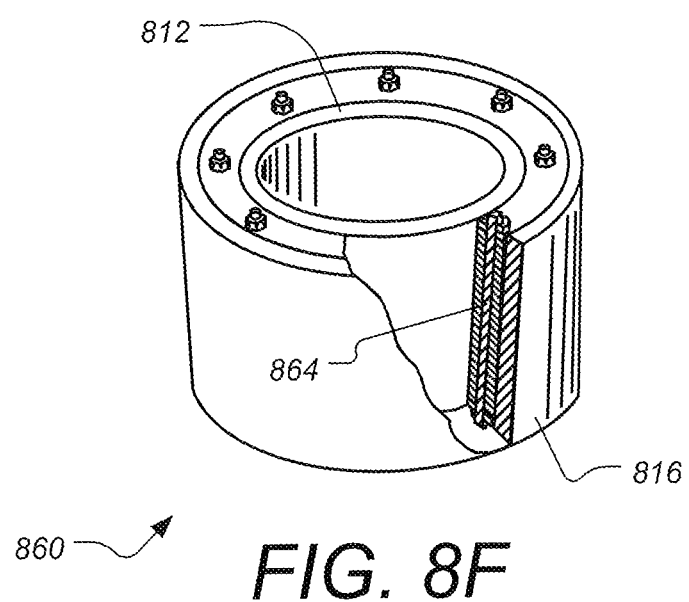
Figure 8G:
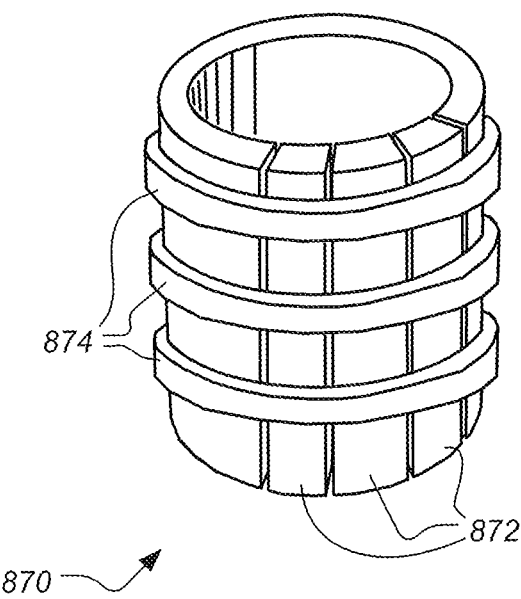

According to some embodiments, an additional sleeve (not shown) can be provided between the porous rock wall 812 and the spheres 844. According to some embodiments, a compliant and compressible sleeve is used to support the outer porous wall. A hydraulic motor such as device 850 shown in FIG. 8E is used to tighten a set of belts or bands around the porous wall assembly (not shown). Referring to FIG. 8F, according to some embodiments, the WCS 860 uses a vertical compressive load applied to a sleeve, for example using a series of rods 864 which causes greater forces against the porous wall 812. In FIG. 8G, WCS 870 uses a plurality of stiff and strong bands 874 around a sleeve or set of slats 872 to support the porous wall (not shown). The set of bands 874 are made using discrete stiffness steps to model a variety of formation stiffness. According to some embodiments, structures other than porous rock wall 812 are used for the various techniques shown in FIGS. 8A-8G. For example, a steel mesh structure can be used such as shown and described elsewhere herein.

Simulating Casing Stiffness and Displacement.

According to some embodiments, casing stiffness and displacement are approximated through the use of the actual casing or components with the same stiffness machined to the same dimensions as common casing sizes. According to some embodiments, thinner cross sections or materials with different stiffness are used and preloaded to bias the casing displacement characteristics to match those of actual casing. With reference to FIG. 4, this can be accomplished by using hydraulic system 302 to control the casing oil pressure to achieve the desired casing displacements. One advantage of biasing the casing displacement with regard to the example embodiments that use actual casing, is that when the casing oil pressure is released a larger displacement of the casing away from the cement can be achieved which can aid in the removal of the cement sheath from the WCS as well as allow for the study of cement to casing adhesion.

Simulating Water Delivery to the Cement.

The permeability of the surrounding formation in the borehole plays an important part in the hydration of the cement, which impacts its dimensions and material properties. In some cases, such as sandstone, the borehole will allow water to move into and out of the formation with ease, thereby satisfying the cement's demand for water. In other cases, such as shale, the formation is largely impermeable and the cement will hydrate using only the water that is used to make the original slurry. According to some embodiments, the WCS delivers water artificially, through discrete locations where the annular chamber has inputs. According to some embodiments, the outer surface of the annular chamber is designed with a surface that behaves like the formation to the cement, but is thin and of controllable permeability for the chamber. A thin membrane may be used which has a very high in-plane water mobility, a porosity to allow water to flow through it yet not cement, and easy access to feed it a controllable amount of water.

Figure 9:
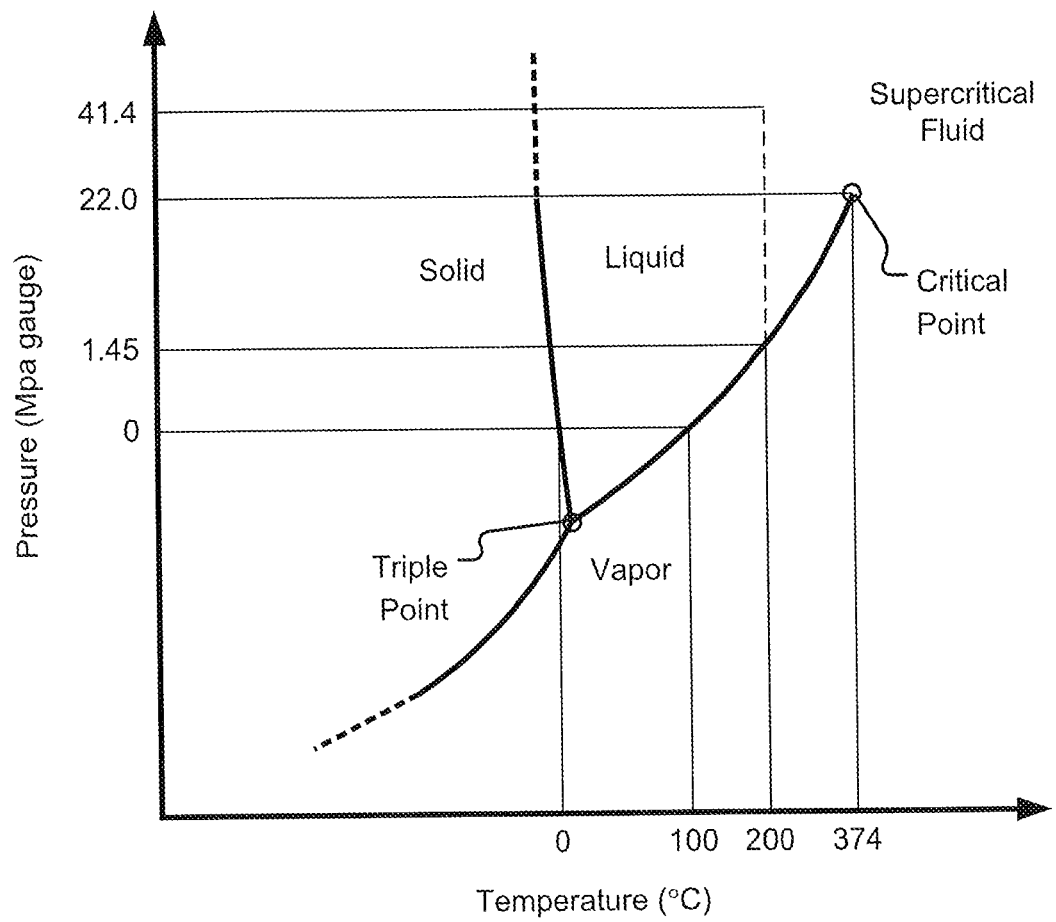
FIG. 9 is a phase diagram for water.

According to some embodiments, the pressure in the chamber can be as high as 6,000 psi, which is 41 MPa. The temperature in the chamber could be as high as 200° C. From FIG. 9, which is a phase diagram for water, it is apparent that for pressures above 1.45 MPa @ 200° C., water is liquid. If the pressure drops to 1.45 MPa, conversion to vapor will start and pressure will remain at 1.45 MPa until all the water boils off; and for temperatures lower than 100° C., the pressure to boil is very low.

Figure 10:
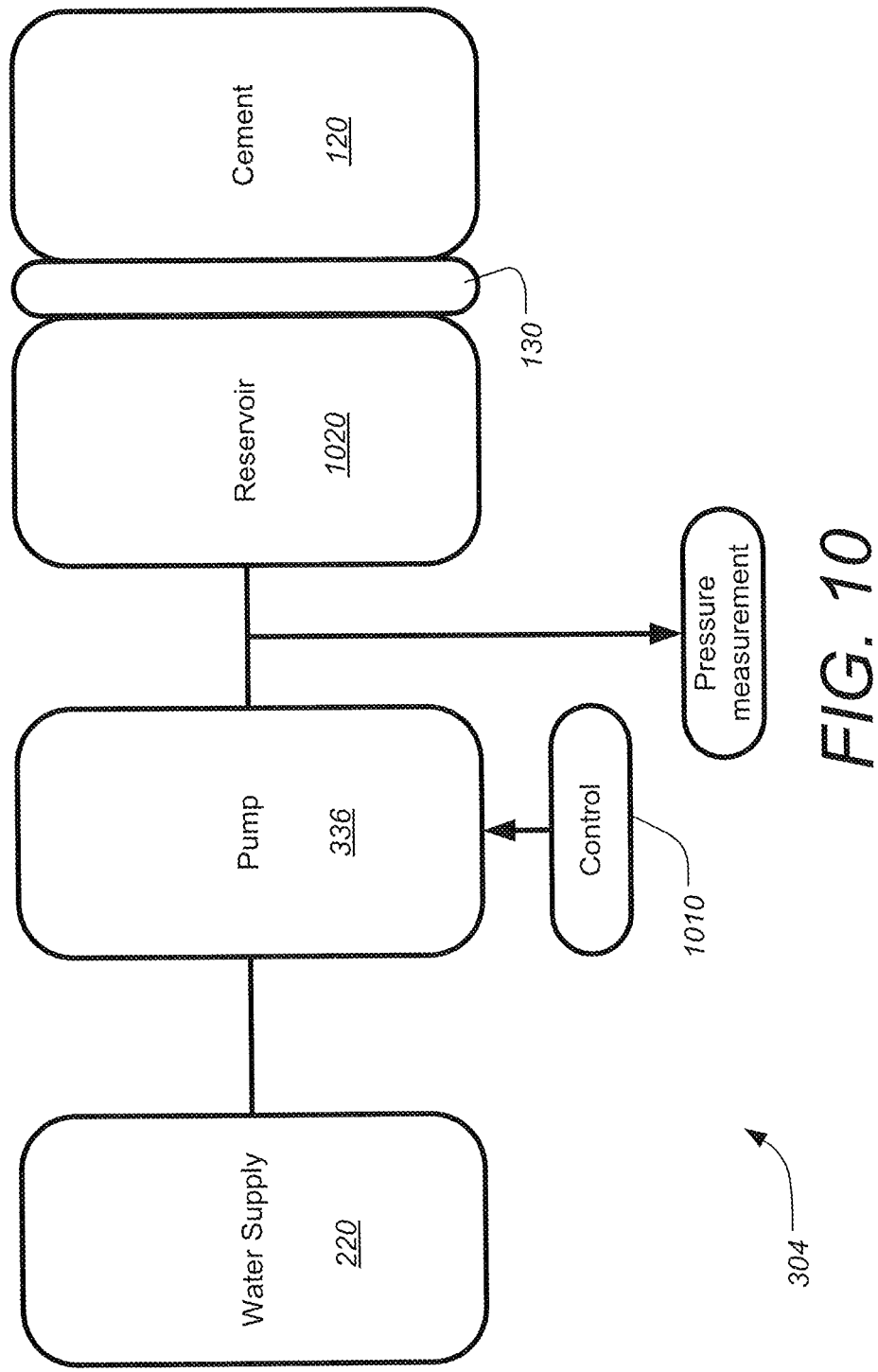
FIG. 10 is a schematic diagram for a water delivery system used with a wellbore cement simulator, according to some embodiments.
Figure 11:
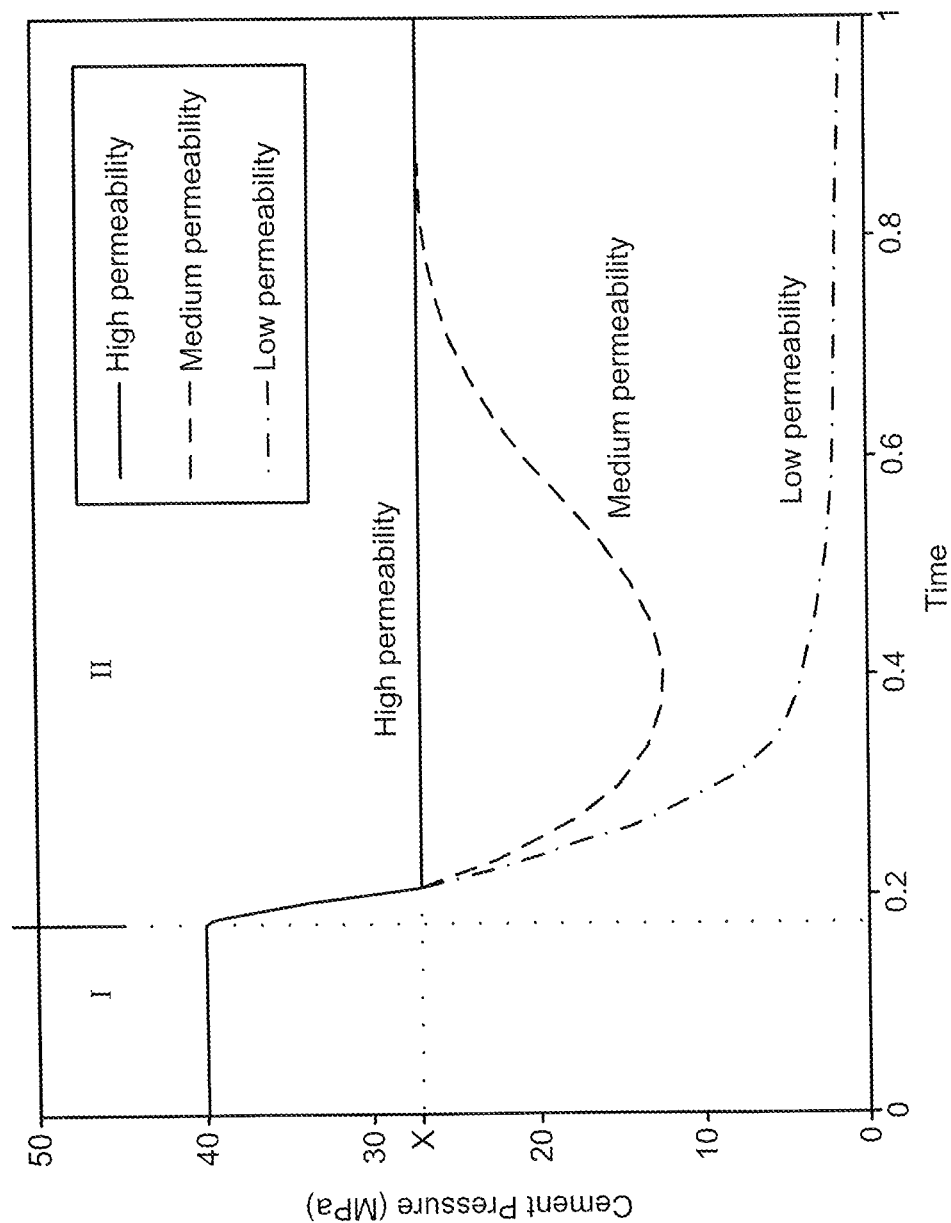
FIG. 11 is a pore pressure diagram for cement as influenced by various types of rock formations, according to some embodiments.

According to some embodiments, a number of assumptions are made regarding the water delivery system. First, the cement has two primary states, the slurry and the hydrated cement. Cement in the slurry state is incapable of supporting shear stress, while cement in the hydrated state is capable of supporting shear stress. Further, the cement is isotropic axially and radially. There is a water usage relationship for the cement, which may be known. FIG. 10 is a schematic diagram for a water delivery system used with a wellbore cement simulator, according to some embodiments. The control system 1010 for water flow is schematically upstream of the water reservoir 1020 contained in the distribution media 130 (e.g. steel mesh or porous rock). From these assumptions, and from research into cement hydration, behavior can be predicted for various types of rock formations as is shown in FIG. 11. FIG. 11 is a pore pressure diagram for cement as influenced by high, medium and low permeability rock formations, according to some embodiments.

It follows that water is approximately incompressible, with respect to the flow rate contemplated. Therefore, when all water in the reservoir is liquid, the control system will work in regulating water delivery regardless of reservoir size or the exact location of the control. When boiling happens, the reservoir has the potential to over-supply the cement with water. Not only is the liquid/vapor combination less viscous than water, but also the amount evaporated is related to the phase diagram and not directly to the flow prescribed by the control. For a slow trickle, where a conversion to vapor could happen, it is useful to monitor the pressure and temperature, and look for conditions indicating vapor. At that point, the reservoir of water is emptied and the controlled water feed is restarted.

For the case of an impermeable formation, the reservoir can be replaced with a solid sleeve, where no water will enter the system. The system will track according to the cement demand and the slurry water supply.

According to some embodiments, the WCS is able to control the hydration of the cement, which has been found to be highly beneficial since this strongly impacts the mechanical characteristics of the cement. There are several challenges in correctly modeling the hydraulic performance of the down-hole formation. A number of different methods for doing so are outlined below. Among the design challenges in this area are providing the range of permeability values of materials. Many orders of magnitude of change in permeability exist between formation rocks and the types of engineering materials that can be used to mimic rock. In the WCS, there is a limited amount of space to provide or take away this water, which makes it important to both distribute the water axially with much greater ease than radially and to keep the reservoir of water outside the cement chamber.

The porous media proxy will also impart its own thermal and mechanical properties to the WCS. The control system should account for the additional energy storage and dissipative elements that the proxy brings which could reduce the accuracy with which the real rock can be modeled. Lastly, the proxy will be in contact with the cement, so the bonding behavior of the cement could be impacted by the adhesion properties and dimensional or surface changes that the cement may experience during the test.

From the analysis of the designs, it is clear that there are two major categories of designs: (1) those that closely match the permeability of the formation, and (2) those that use flow control to mimic the permeability. FIGS. 12A-12H are diagrams illustrating certain aspects of various water delivery techniques for use in wellbore cement simulators, according to some embodiments. Each of these techniques has its own advantages in terms of its ability to distribute water in a controlled and even manner. The example embodiment of the WCS disclosed above uses the multi-layer mesh similar to the technique shown in FIG. 12F.

Figure 12A:
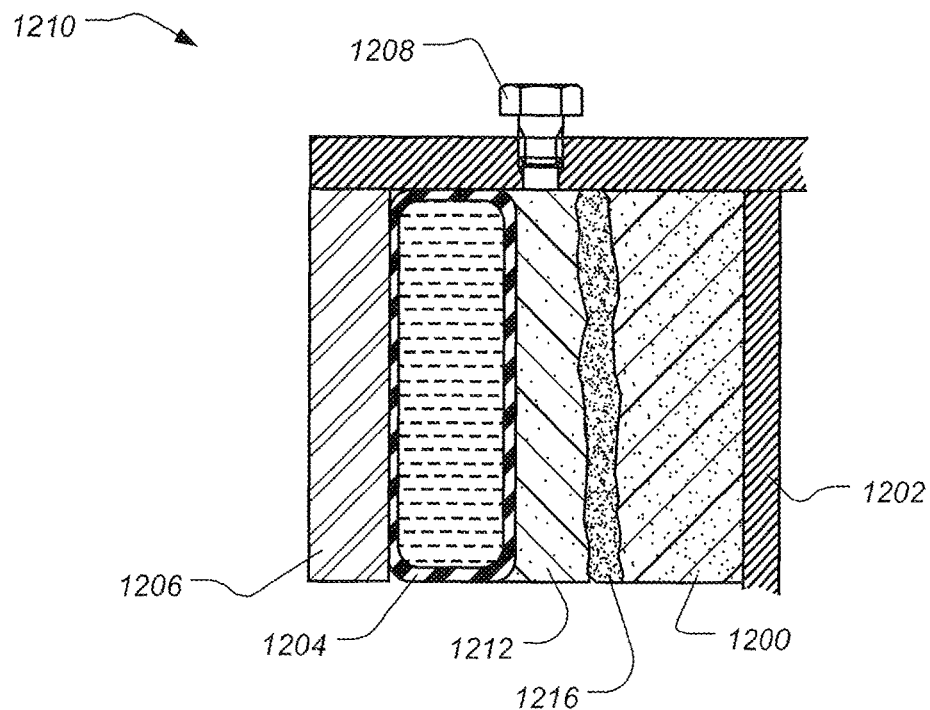
Figure 12B:
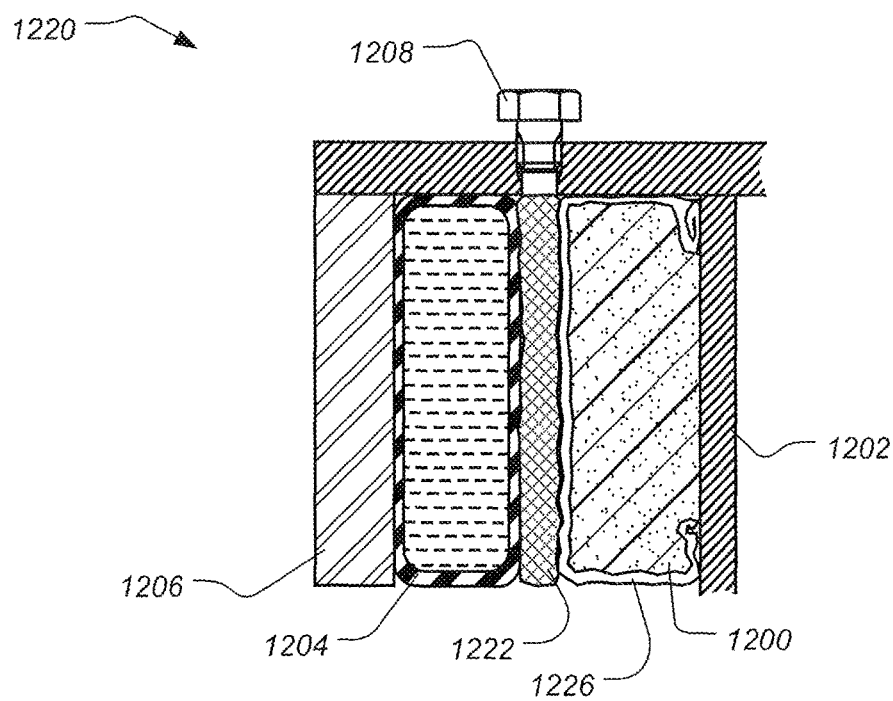
Figure 12F:
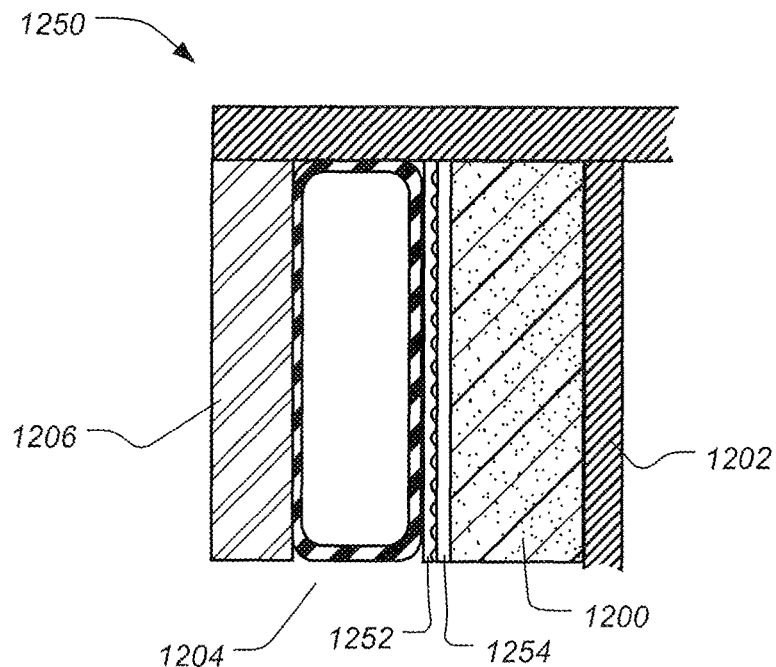
Figure 12G:
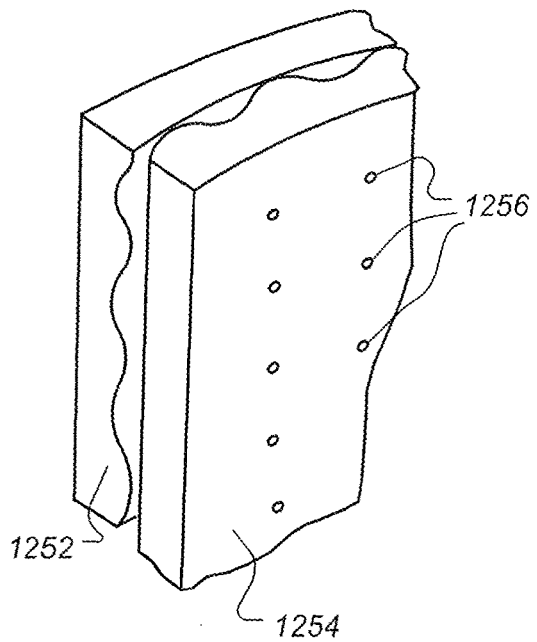
Figure 12H:
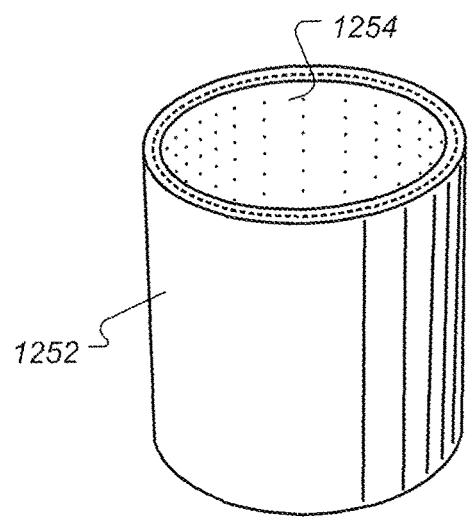

In FIG. 12A WCS 1210 uses clay 1216 to simulate the permeability of the actual formation rock. Certain clay formations have very low permeability values, so the back of the clay 1216 is supported by a high permeability particle layer 1212 that allows an even distribution of the water supplied via port 1208. The hydraulic-oil-filled bladder 1204 supplies the pressure and is confined by outer containment wall 1206. The cement annulus 1200 is shown between the clay 1216 and casing wall 1202. In FIG. 12B, WCS 1220 uses a fine mesh high strength bag 1226 to contain the cement 1200. A porous mesh 1222 that allows an even distribution of water supports this bag 1226. The bag 1226 is attached to the casing 1202 at the top and bottom as shown. In FIG. 12C, WCS 1230 uses a wound tube 1232 that is crushed to give it a high strength rectangular profile with a small void space 1234 in the center (shown in FIG. 12D). The tube 1232 also has small holes 1236 perforated on the inside to allow the system to feed water to the cement 1200. In FIG. 12E, WCS 1240 uses coated sand 1242 that is packed into a tube shape, or pre-made into a tube shape. The sand 1242 has very high permeability, so water flows through it very easily and also has very even wicking qualities. In FIG. 12F, WCS 1250 uses a pair of metal sleeves 1252 and 1254, the latter having perforated holes 1256 to distribute the water. The sleeves 1252 and 1254 have a corrugated surface in patterns that are orthogonal to each other as shown in FIG. 12G that forms a cavity between them. FIG. 12H shows the combination structure that is formed by the combination of sleeves 1252 and 1254. According to some embodiments, one, two or more layers of steel mesh are used instead of the sleeves 1252 and 1254, such as shown in FIG. 1. According to some embodiments, a WCS is made in a modular fashion that allows for one or more different water delivery techniques, such as shown in FIGS. 12A-12H, depending on the particular rock formation characteristics that is being simulated.

Sensing Features.

According to some embodiments, further description will now be provided on several technologies that may be used for collecting data on temperature, pressure, strain, hydration state, and cement damage.

Pore Pressure (Formation and Cement) Sensing.

According to some embodiments, pressure profile measurements (pore, confining/overburden, and hydrostatic) are achieved using one or more of the following: (1) optical fiber probes; (2) acoustic shear and compression wave velocities as a function of confining pressure; and (3) nanoparticles or fibers sensed by Acoustic Electrical Impedance Tomography (AEIT). The Rice and Cleary theory of poroelasticity, involving the drained and undrained bulk modulus constants, and the Biot coefficient, may be simulated by the various configurations of the WCS system. According to some embodiments, a pore pressure map throughout the annulus is obtained using techniques analogous to medical applications where combined through-transmitted ultrasound tomography and backscattered elastography allows for the determination of the shear and Young's moduli, the bulk modulus (from the two sound velocities), and the Poisson's ratio.

According to some embodiments, three technologies that can be used alone or in combination with one another for determining pore pressure include: (1) electrical impedance 3D tomography; (2) ultrasound—nonlinear phased array; and (3) optionally—sensing particles (fibers and conducting composite particles). The combination of electrical impedance and ultrasound capabilities, supplemented by optical fibers and smart fibers or particles, can provide a reasonable low-risk means for pressure sensing in the WCS. According to some embodiments, one or more other techniques may be used, including ultrasound methods which begin with time of flight experiments, progress to tomographic measurements, followed by non-linear detection, and finally are combined with electrical tomography and non-linear electrical impedance methods.

Sensing Hydration Progress.

Ultrasonic transit time is a well-established method for determining the hydration progress of cement. According to some embodiments, this technology is used to provide a measure of a cement sample's compressive strength development over time while it is being cured under downhole temperature and pressure conditions.

Similarly, according to some embodiments, the WCS can utilize a pair of custom piezo-ceramic transducers in contact with the cement to measure shear and compressional wave velocities, which change as a function of the degree of hydration as the cement evolves from a slurry to a solid. Use of the compressional and shear speeds allows for the determination of Young's modulus and Poisson's ratio of the cement which are particularly valuable for predicting the response of acoustic measurement in cemented cased holes as well as potentially predicting the mechanical integrity of the cement sheath during the life of a well.

Sensing Cement Temperature.

According to some embodiments, cement temperature in the WCS is sensed using thermocouples and/or fiber optics. In some cases, temperature measurements on the boundary of the cement annulus are sufficient to understand the gradients that exist in the interior. According to some embodiments, the exothermic cement reaction is detected as a change in the heat flux required in the oil reservoir control. Since temperature probes are relatively inexpensive, a sparse array of disposable sensors is used in the WCS, according to some embodiments.

Sensing Cement Strain.

Figure 13A:
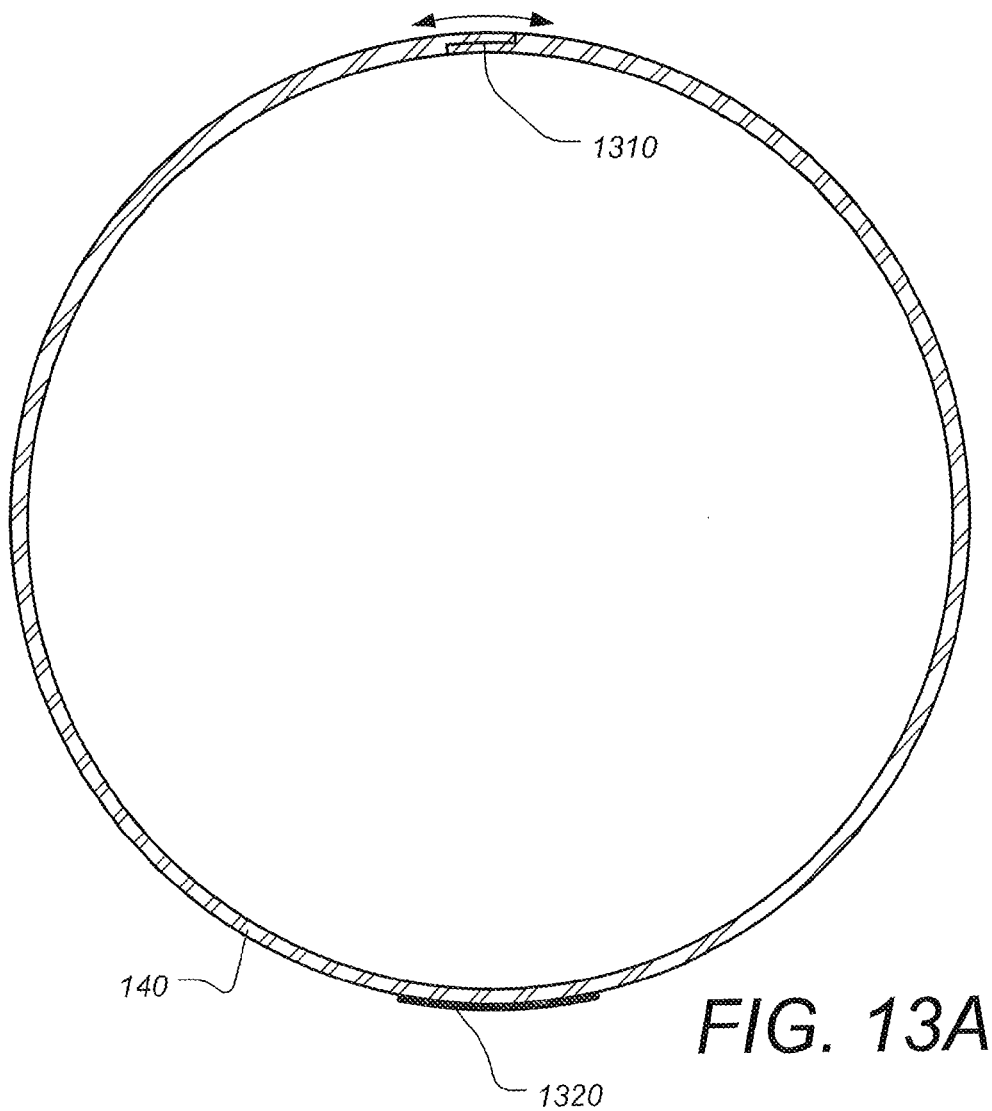
FIGS. 13A and 13B are cross sectional views illustrating a technique for sensing cement strain, according to some embodiments.
Figure 13B:
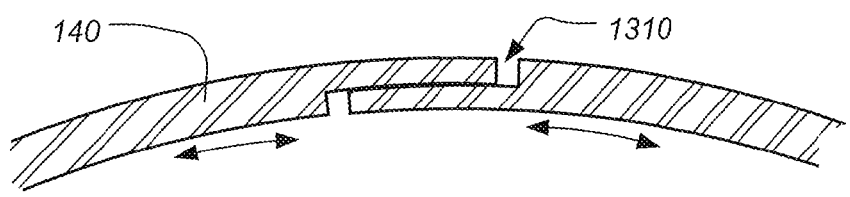
Figure 14:
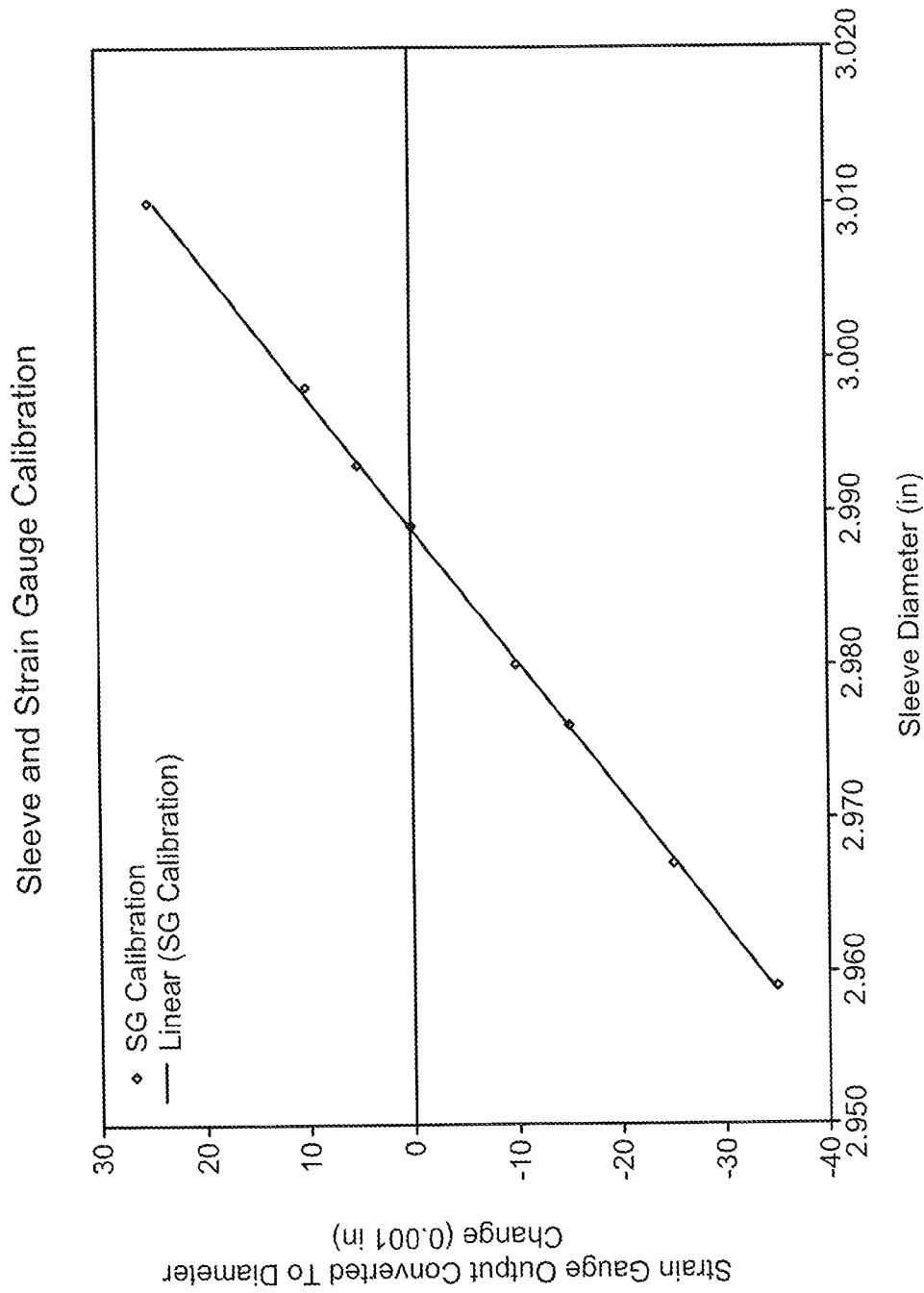
FIG. 14 is a plot showing an example of the linear relationship between the strain gauge reading and changes in the sleeve diameter, according to some embodiments.

FIGS. 13A and 13B are cross sectional views illustrating a technique for sensing cement strain, according to some embodiments. Stainless steel sleeve 140 surrounds the cement (e.g. as shown in FIG. 1). An axial slit 1310 allows the sleeve 140 to expand or contract with the cement due to a variety of thermo-mechanical loading conditions including changes in the confining oil pressure (simulating the formation pressure), cement hydrostatic pressure, and casing oil pressure. A plurality of strain gauges 1320 is placed along the sleeve 140 to measure various axial and circumferential locations. Strain gauge readings can be directly correlated to changes in the sleeve diameter and thus provide an accurate measurement of cement strain under various loading conditions. It has been found that locating the strain gauges 1320 directly opposite the axial slit 1310 provides for an accurate determination of sleeve diameter. FIG. 14 is a plot showing an example of the linear relationship between the strain gauge reading and changes in the sleeve diameter, according to some embodiments. In the case shown in FIG. 14, the strain gauges were located opposite the axial slit as shown in FIG. 13A. It should be noted that even though the strain gauges 1320 are located on the outer surface of the sleeve 140, they are protected from the simulated downhole environment including contact with the cement. According to some embodiments, the strain gauges can be located at the slit 1310.

Sensing Casing Strain.

According to some embodiments, casing strain is also measured using commercial strain gauges placed directly on the casing itself. The inner surface of the casing is readily accessible for sensing casing strain in the WCS. As the inner volume of the casing will be full of hot, pressurized oil, suitable strain gauges are selected that will work in this environment.

Crack and Micro-Annulus Formation.

A number of measurement technologies can be used with the WCS to detect crack and micro-annulus formation. Further detail of an active acoustic technique will now be provided, according to some embodiments.

Pulse-Echo & Pitch-Catch Measurements.

Ultrasound measurement technologies use high frequency sound waves for imaging purposes with good spatial resolution. Lower frequency ultrasound penetrates further, but results in lower spatial resolution. Pulse-echo and pitch-catch tools for wellbore imaging cover a wide range of measurement modalities in the frequency range of 100-1000 kHz and with transducer alignment angles from 0 degrees (normal incidence) up to 40 degrees they are able to resolve features with characteristic lengths of about 1 cm and fracture widths on the order of 100 microns.

Figure 15:
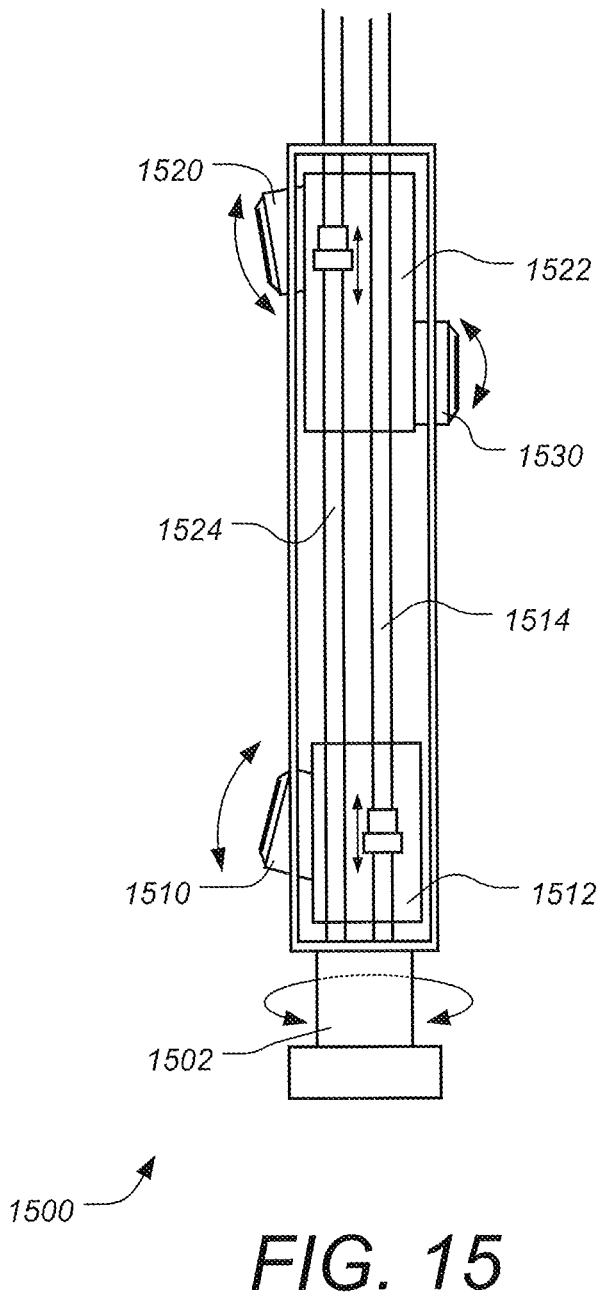
FIG. 15 is a diagram illustrating certain aspects of an ultrasonic measurement tool for use with a wellbore cement simulator, according to some embodiments.

FIG. 15 is a diagram illustrating certain aspects of an ultrasonic measurement tool for use with a wellbore cement simulator, according to some embodiments. Ultrasonic measurement tool 1500 uses three separate transducers 1510, 1520 and 1530 for pulse-echo and pitch-catch modes. Such a measurement operates adequately within the height limits of the WCS without perturbation from reflections taking place at the sample edges as these will arrive outside of the temporal window of interest.

The ultrasonic measurements are based on exciting and detecting "Lamb-wave"-like modes in the casing whose attributes provide the capabilities to probe two characteristics of interest for wellbore integrity: (1) the nature and mechanical properties of the annular fill between casing and rock, and (2) the bonding state at the casing-cement interface and, potentially, at the cement-formation interface.

The operational range of these measurements includes the well-established UltraSonic Imager (USI) pulse-echo and pitch-catch modes. According to some embodiments, additional modalities can be used to minimize the uncertainty on the results especially with respect to the casing-cement bond quality. USI may be used to monitor the formation and evolution with time of the compressive and tensile strengths of the cement slurry as it sets into a solid.

According to some embodiments, the ultrasonic measurement device 1500 for the WCS contains three acoustic transducers 1510, 1520 and 1530. Transducer 1510 is mounted on single transducer trolley 1512 that can be moved up and down along lead screw 1514. Similarly, transducers 1520 and 1530 are mounted on dual transducer trolley 1522 and can be moved up and down along lead screw 1524. The device 1500 has three degrees of freedom: axial position and axial transducer separation via movement of the trolleys 1512 and 1522, and azimuthal rotation via movement of the rotatable base 1502. The transducer axial spacing is adjustable. The transducer angles are infinitely adjustable from 20-40 degrees. To simulate a logging mode, rotational speeds up to 20 RPM and linear speeds up to 50 mm/s are achievable. Brushless DC motors with programmatic control drive motions on all three axes. According to some embodiments, the angle of each of the transducers can also be adjusted.

As an alternative to using isolated transducers with mechanical means for continuous or discrete alignment to excite and detect various Lamb modes in the casing, according to some embodiments the measurement can be implemented using an ultrasonic phased array. The convenience of steering acoustic beams provides for a rich measurement whereby data from multiple Lamb modes with various particle displacement characteristics are used for an effective inversion-based interpretation. The combination of measurements from transducers in contact with the cement sheath and measurements done through casing may provide more effectively, properties of the cement sheath separately from the bonding conditions at the casing interface and potentially at the formation wall.

Other Measurement Technologies.

As noted above a number of other measurement technologies can be used to measure various aspects of the cement sheath during and after curing, including the detection of defects and/or damage in the cement sheath. These measurements generally fall into the broad categories of electromagnetic, acoustic, hybrid EM-acoustic and "other" methods. Electromagnetic measurement methods which can be used include: electrical impedance (EIS) and electrical impedance tomography (EIT); electrical capacitance tomography (ECT); magnetic induction tomography (MIT); microwave (e.g. microwave resonant cavity); and magnetic resonance imaging (MRI). Hybrid Multi-Physics measurement methods that can be used include: magnetic resonance electrical impedance tomography (MREIT); acoustic electrical impedance tomography (AEIT); magnetoacousto-electric tomography (MAET); acoustic methods; ultrasonic (e.g. EIT-US; active ultrasound, synthetic aperture focused tomography ultrasound (SAFT US), linear resonant ultrasound (RUS)); and passive acoustic emission microsiesmogram, non-linear acoustic methods. "Other" measurement methods that can be used include: X-Ray computed tomography (X-Ray CT, micro X-Ray CT and holographic X-Ray CT); neutron tomography (NI); and thermocouple techniques, optical Bragg grating fiber, smart particles/fibers (e.g. smart concrete carbon fiber, pore and matrix pressure sensing particles).

Non-invasive methods, such as EIT and US capability each use modalities to achieve microcrack/delamination imaging, as well as hydration state in some cases. Non-linear studies can follow on initial linear studies for both EI and US technologies. Furthermore, a hybrid method may also be considered. According to some embodiments, these methods are can also be supplemented by minimally invasive probes.

The bulk properties of the cement can be interrogated by variations in 1) electrical, 2) mechanical (pressure waves), or 3) density values. Electrical conductivity (or resistivity) will change if there is a change in the microstructure, such as pore connectivity or tortuosity during hydration or the formation of a crack. Magnetic methods, relying on eddy currents, also will have this behavior. Similarly, these types of changes will affect the velocity of sound. In particular, the shear and compression waves will be affected. Microcracks or other damage such as delamination will change the material to introduce nonlinearities in both the electrical and mechanical characteristics—that is, non-linear effects may be strong indicators of damage and defects. Both electrical and mechanical values may be acquired in a tomographic fashion, thereby locating regions of defects. More straightforward conceptually is the imaging of density via x-ray or neutron absorption. Resolving individual microcracks in the WCS chamber is unrealistic since the average density within a voxel will not significantly change unless the voxel size is on the order of the microcrack. For this reason, the electrical and mechanical methods may be more sensitive to microcrack formation.

Example Experimental Procedure

Figure 17:
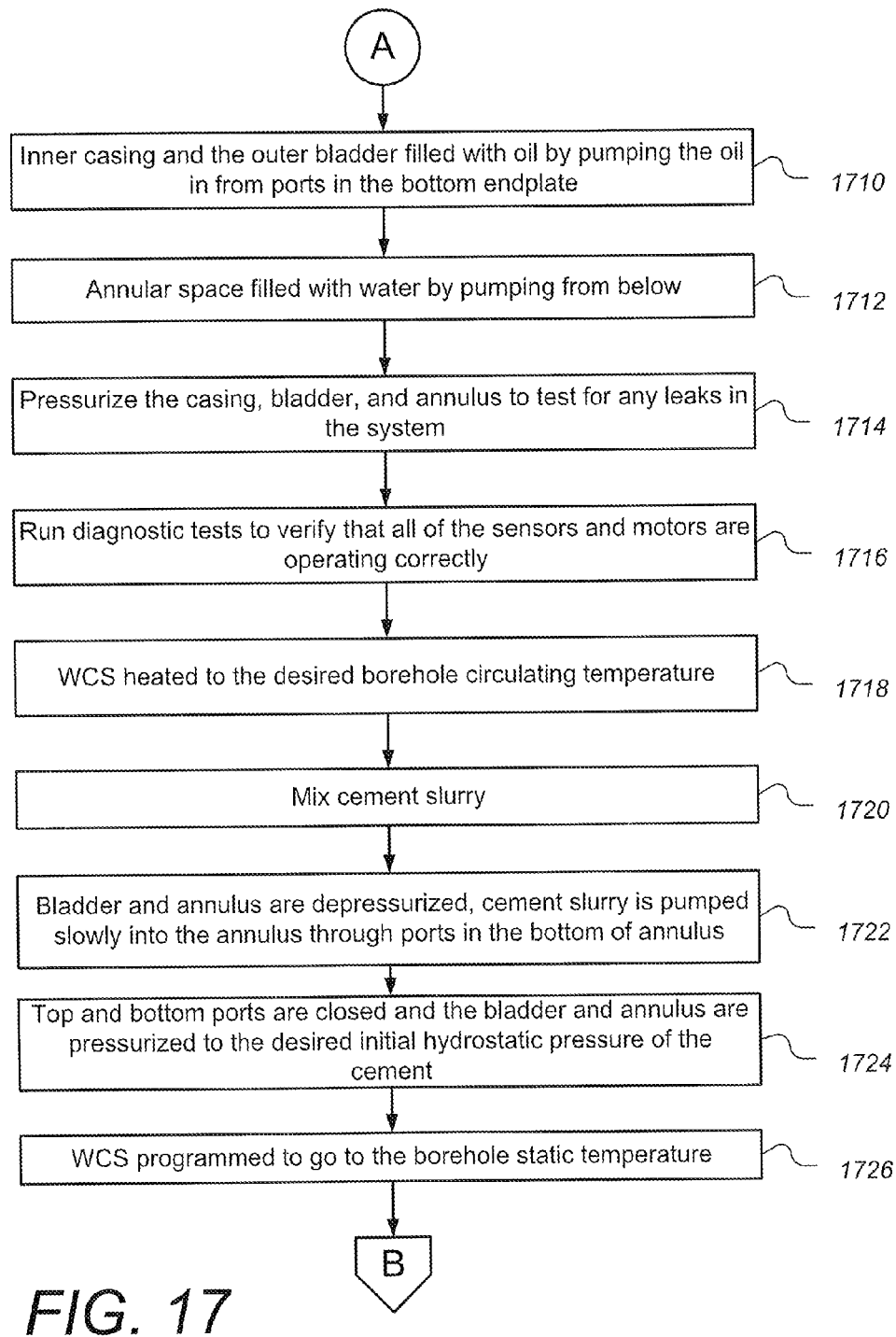
Figure 18:
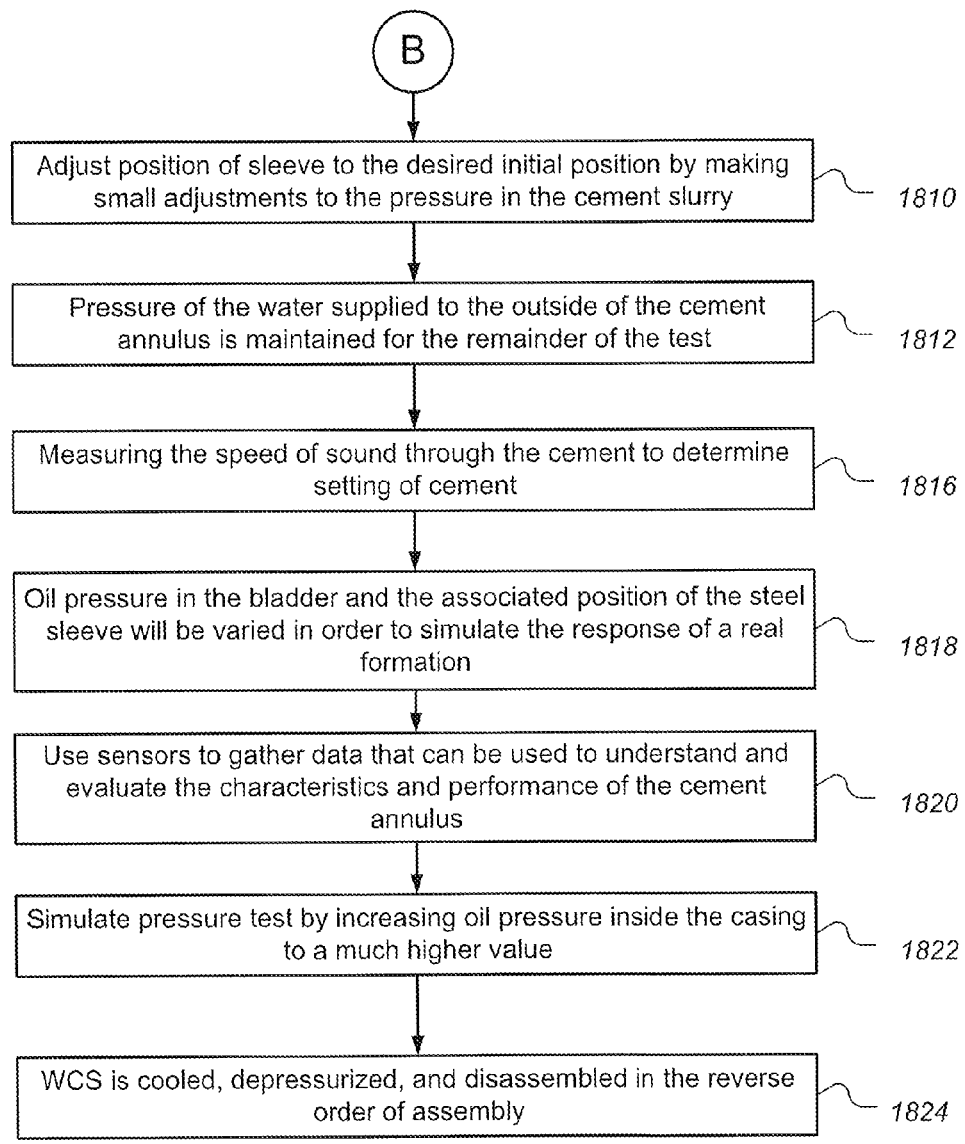

FIGS. 16, 17 and 18 are a flow chart illustrating aspects of an example test procedure of simulating wellbore cementing against a permeable formation and then conducting a pressure test, according to some embodiments. The device would first be prepared for the test by performing as follows. Referring to FIG. 16, the bottom endplate of the pressure vessel acts as the focal point for assembly. In block 1608, thermal couples are used to measure the casing and cement pressure. In block 1610, the ultrasonic logging tool with associated movement motors is mounted at the center point of the bottom endplate. Then, in block 1612, the inner casing is lowered into place with a lifting crane and sealed to the bottom endcap, and in block 1614 the wires for the inner strain gauges and hydration sensors are connected to feedthroughs in the bottom endcap. In some cases blocks 1612 and 1614 can be combined, for example making the wire connections as the casing is being lowered before it makes its seal with the radial o-ring in the end cap. The bottom gap filler ring can be installed at this point. In block 1616, the layers of wire mesh that facilitates water delivery to the cement can be placed inside the steel sleeve. In block 1618, the steel sleeve that defines the outer position of the cement annulus is then put in place, and wires for the outer strain gauges are connected to feedthroughs in the bottom endcap. The annular space between the inner casing and the steel sleeve defines the geometry of the cemented annulus.

Next, in block 1620, the bladder assembly, comprising the elastomer bladder and its support frame, is placed around the steel sleeve. The bladder will fit close to the steel sleeve, so that as soon as it is slightly pressurized it will press against the outside of the steel sleeve. The top gap filler ring can now be installed. Then, in block 1622, the cylindrical body of the pressure vessel, with associated heating bands and insulation, is lowered into place with a lifting crane and connected to the bottom endplate. The method of connecting the endcaps to the pressure vessel will depend on the design of the pressure vessel, which in turn will depend on the pressure rating. In block 1624, the top endcap will next be lowered into place with a lifting crane. The top endcap will seal against the inner casing and be connected to the body of the pressure vessel.

Referring next to FIG. 17, in block 1710, the inner casing and the outer bladder will be filled with oil by pumping the oil in from ports in the bottom endplate. Note that the systems for filling and pressurizing the bladder and the casing are independent, and the type of oil need not be the same. In block 1712, the annular space will be filled with water, also by pumping from below. Alternatively, the annulus can first be filled manually from above with a different type of fluid such as drilling mud, and then a small amount of water added from below. Care is taken during filling to eliminate air from all parts of the system (e.g. vibration can be used). In block 1714, the casing, bladder, and annulus are pressurized to test for any leaks in the system. At this time, in block 1716, diagnostic tests can be run to verify that the sensors and motors are operating correctly. When the device is determined to be operating correctly, in block 1718, it can be heated to the desired borehole circulating temperature.

When the device has reached the desired temperature, in block 1720 the cement slurry can be mixed. The slurry formulation and mixing method will vary according to the specific test being performed. The volume of cement slurry that is prepared should slightly exceed the volume of the annulus. After mixing, in block 1722 the bladder and the annulus are depressurized and cement slurry is pumped slowly into the annulus through ports in the bottom annulus, displacing the previous fluid through ports in the top endcap. When the annulus is completely filled with cement, in block 1724 the top ports (and bottom ports for the cement annulus) are closed and the bladder and annulus are pressurized to the desired initial hydrostatic pressure of the cement, assumed here to be 1500 psi. For this example, the pressure inside the casing is initially kept close to ambient pressure, in order to have maximal ability to expand the casing later in the test. In block 1726, the WCS can now be programmed to go to the borehole static temperature, if different from the circulating temperature.

Referring to FIG. 18, in block 1810 while the cement is in the slurry state, the pressure in the bladder and the pressure in the slurry will be equal because the steel sleeve will expand or contract to eliminate any pressure differential. The position (i.e. diameter) of the sleeve is known from the outer strain gauges. The position of the sleeve can be adjusted to the desired initial position by making small adjustments to the pressure in the cement slurry (e.g. by releasing or adding either cement or oil to affect a change on the sleeve's diameter). The sleeve should initially be in an intermediate position, so that both expansion and shrinkage of the cement during the test can be measured without reaching either the maximum or minimum sleeve diameter. For this example, a permeable, water-filled formation is simulated, so in block 1812 the pressure of the water supplied to the outside of the cement annulus is maintained at 1500 psi for the remainder of the test.

Once the cement has set, the oil pressure in the bladder and the water pressure supplying the cement are no longer linked. Setting of the cement can be determined in a number of ways, with the primary method being the hydration sensors measuring the speed of sound through the cement as shown in block 1816. Once the cement has set, in block 1818 the oil pressure in the bladder and the associated position of the steel sleeve will be varied in order to simulate the response of a real formation. More specifically, the pressure in the bladder can be programmed to decrease if the sleeve diameter decreases (cement shrinkage). The relationship between bladder pressure and sleeve position depends on the type of formation that is being simulated. One possibility is to assume an elastic response of the formation with a fixed stiffness value, but other relationships are possible. The formation response to be simulated will be determined prior to the run and programmed into the WCS.

As the cement hydrates, in block 1820 sensors will gather a variety of data that can be used to understand and evaluate the characteristics and performance of the cement annulus. These include, but are not limited to, the temperature of the cement, the pore pressure inside the cement, the shrinkage or expansion of the cement (from the inner and outer strain sensors), the compressive strength of the cement (from the hydration sensors), and the quality of the bond between the cement and the casing (from the ultrasonic tool inside the casing).

In the present example, a wellbore pressure test is simulated. Pressure tests are often conducted after cementing the well to ensure that there is no communication between the reservoir and the inside of the casing. A pressure test comprises, in simplest form, of increasing the pressure inside the casing and then watching to see how fast the pressure declines. A problem with pressure tests is that they slightly expand the casing, which can put the cement in tension possibly causing it to crack or de-bond either during the test or after the pressure is returned to the original value. In this example, in block 1822 after the cement is fully set after a period of 2-3 days, the oil pressure inside the casing is increased to a much higher value, such as 6000 psi. As the pressure is increased, the hydration sensors and logging sensors are put in a listening mode to listen for acoustic events such as cracking and debonding of the cement. In addition, ultrasonic logging can be conducted both during the pressure test and after the casing pressure has returned to the original value, to see if the cement has debonded from the casing.

After the test is complete, in block 1824 the WCS is cooled, depressurized, and disassembled in the reverse order of assembly. The cemented annulus will most likely be firmly attached to the inner casing. Removal of the cement can be accomplished by pushing the casing through the cement using a specialized press, or by cutting and chiseling the cement away from the casing in pieces. Further testing of the cement can then be conducted if wished.

The cement hydration reactions generate a water demand inside the cement sheath resulting in a drop in pore pressure. This will cause bulk shrinkage (primarily before set) and internal stresses (during/after set), unless water flows into the sheath from the formation. According to some embodiments, with the WCS, the same slurry formulations can be hydrated under conditions of full water access, no water access, and partial water access (flow rate is insufficient to meet the demand when cement is hydrating rapidly). Measurements of the cement pore pressure, movement of the cement/formation interface, and other aspects of the cement response can be made in each case. This data, obtained for different formulations and at different temperature and pressure conditions, can provide important information about the sealing ability of the cement against different types of formations. The data can also provide new insights into the logging response under different conditions. The data can further be used to validate new poro-mechanics based models of cement hydration.

The mechanical properties of the formation in contact with the outside of the cement sheath will affect the stress state, volume changes, and sealing ability of the cement. If the cement shrinks radially due to the hydration process, the formation will unload to "follow" the cement. The extent to which this occurs depends on the stiffness of the formation and the initial stress state of the formation. According to some embodiments, the WCS is able to simulate this formation movement by means of a split steel sleeve surrounding the cement and fitted with strain gauges. A pressurized oil bladder pushing on the sleeve can control the movement of the "formation" in response to feedback from the cement pore pressure, strain gauges, etc. Experiments can be conducted to simulate various formation types, as well as cementing between two casings, while measuring the resulting changes in the cement pore pressure profile, debonding/microannulus formation, and logging response.

A standard procedure after completing a well is to test for leaks by overpressuring from the surface and then watching the pressure decay curve. The overpressure will expand the casing, putting the cement sheath into tension from a hoop stress, possibly causing debonding and/or tensile failure, but the exact effect of a pressure test on the cement is difficult to predict with the current state of knowledge/models. According to some embodiments, a WCS is able to simulate a pressure test directly, on a cement sheath that has been hydrated in place under realistic conditions, and which is instrumented with strain sensors on the outer surface. The logging response before, during, and after the pressure test will provide indications of the extent of damage (if any) resulting from the test. Passive acoustic sensors can detect the time (and associated casing pressure) at which a debonding or cracking event occurs.

The use of expanding cement formulations has been identified as a promising route to improve the ability of the cement sheath to resist cracking, debonding/microannulus formation, and improve logging response. The use of expanding formulations in the WCS, according to some embodiments, allows the performance to be measured directly under realistic conditions. The prestress conditions (internal stress caused by confined expansion) can be measured directly under a variety of wellbore conditions. In addition, the ability of an expanding formulation to compensate for radial movement of the formation or casing, or to close an inner or outer microannulus, can be tested.

Some of the methods and processes described above, including processes as listed above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above, as listed above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method for simulating a wellbore cementation procedure of a downhole annular region between a casing and a formation wall, the method comprising:
   placing an unset cement sample into an annular simulation volume defined at least in part by an inner annular surface representing an outer surface of the casing and by an outer annular surface representing an inner surface of the formation wall, wherein a fluid-filled outer volume is defined by a compliant member disposed radially outside the outer annular surface, and wherein the outer annular surface is configured to be radially displaceable by controlling pressure of said fluid-filled outer volume thereby simulating radial displacement of the formation wall;
   making one or more measurements during hydration of the placed cement sample; and
   determining one or more properties of the cement sample based at least in part on the one or more measurements.

2. The method according to claim 1 wherein the outer annular surface is further configured to be radially displaceable such that the outer annular surface simulates formation wall responses to cement pressure and cement volume changes for a plurality of formation stiffness values.

3. The method according to claim 2 wherein oil fills said fluid-filled outer volume and said method further comprising hydraulically controlling pressure of the oil that fills said fluid-filled outer volume to simulate formation wall responses to cement pressure and cement volume changes.

4. The method according to claim 1 wherein oil fills said fluid-filled outer volume and said method further comprising hydraulically controlling pressure of the oil that fills said fluid-filled outer volume to simulate radial displacement of the formation wall.

5. The method according to claim 1 further comprising controlling temperature of fluid contained in said fluid-filled outer volume to simulate downhole temperature conditions.

6. The method according to claim 1 wherein the outer annular surface is at least partially supported using one or more techniques selected from a group consisting of: a fluid-filled flexible metal shell, a coiled compliant high-pressure hydraulic conduit, a set of sleeves having various stiffnesses, a set of discrete spherical solid objects positioned within a confined outer volume, a set of hydraulically controlled circumferentially positioned bands of material, a compliant compressible sleeve confined by a rigid outer wall and can be adjusted by applying pressure in an axial direction, and a set of slats circumferentially surrounded by a plurality of bands.

7. The method according to claim 1 further comprising controlling temperature and pressure of a fluid contained in an inner chamber within the inner annular surface.

8. The method according to claim 7 further comprising radially displacing said inner annular surface by controlling the pressure of the fluid contained in said inner chamber.

9. The method according to claim 8 wherein said radially displacing said inner annular surface simulates pressurized mud and cement in said casing.

10. The method according to claim 8 wherein said radially displacing said inner annular surface simulates a casing pressure test conducted after cement setting.

11. The method according to claim 1 further comprising delivering water into the annular simulation volume during hydration of the placed cement thereby simulating water delivery to the cement from the formation wall.

12. The method according to claim 11 wherein the water delivering is facilitated by one or more structures selected from a group consisting of: one or more metallic mesh members circumferentially positioned on the outer annular surface, a layer of porous rock material circumferentially positioned on the outer annular surface, a layer of foam material circumferentially positioned near the outer annular surface, a coiled flattened conduit having perforations and being positioned on the outer annular surface, and two or more layers of material being textured to allow water flow and being circumferentially positioned on the outer annular surface.

13. The method according to claim 1 wherein said one or more determined properties are selected from a group consisting of: pore pressure, hydration progress, cement temperature, cement strain, casing strain, crack formation, and micro-annulus formation.

14. The method according to claim 1 wherein said one or more determined properties includes pore pressure of the cement, and said making one or more measurements are selected from a group consisting of: electrical impedance 3D tomography; ultrasound; and particle sensing.

15. The method according to claim 1 wherein said one or more determined properties includes cement strain which is based in part on strain gauge measurements made on an outer sleeve of material which at least in part forms the outer annular surface.

16. The method according to claim 1 wherein said one or more determined properties includes formation of cracks and/or a micro-annulus, and said one or more measurements includes ultrasound measurements.

17. The method according to claim 16 wherein said ultrasound measurements are pulse-echo and pitch-catch measurements made using a plurality of ultrasonic transducers positioned within the inner annular surface.

18. A method of cementing a wellbore comprising carrying out a cementation procedure that has been simulated according to the method of claim 1.

19. A wellbore cemented according to cementation procedure simulated according to the method of claim 1.

20. A method for simulating a wellbore cementation procedure of a downhole annular region between a casing and a formation wall, the method comprising:
placing an unset cement sample into an annular simulation volume defined at least in part by an inner annular surface representing an outer surface of the casing and by a water permeable sleeve positioned against an outer annular surface representing an inner surface of the formation wall;
delivering water into the annular simulation volume via the water permeable sleeve during hydration of the placed cement thereby simulating water delivery from the formation wall to the placed cement;
making one or more measurements during hydration of the placed cement sample; and
determining one or more properties of the cement sample based at least in part on the one or more measurements.

21. The method according to claim 20 wherein a rate of water delivered from a water source to the water permeable sleeve is controlled so as to simulate water delivery from the formation wall to the cement.

22. The method according to claim 20 wherein the outer annular surface is configured to be deformable which simulates radial displacement of the formation wall in response to cement pressure and cement volume changes.

23. The method according to claim 20 further comprising:
controlling temperature and pressure of a fluid contained in an inner chamber within the inner annular surface; and
radially displacing said inner annular surface by said controlling the pressure of the fluid contained in said inner chamber.

24. The method according to claim 20 wherein said one or more determined properties are selected from a group consisting of: pore pressure, hydration progress, cement temperature, cement strain, casing strain, crack formation, and micro-annulus formation.

25. A system for simulating a wellbore cementation procedure of a downhole annular region between a casing and a formation wall, the system comprising:
an annular simulation volume defined at least in part by an inner annular surface representing an outer surface of the casing and by an outer annular surface representing an inner surface of the formation wall, wherein a fluid-filled outer volume is defined by a compliant member disposed radially outside the outer annular surface, and wherein the outer annular surface is radially displaceable by controlling pressure of said fluid-filled outer volume thereby simulating radial displacement of the formation wall; and
a measurement system including a plurality of sensors configured to make one or more measurements during hydration of a cement sample placed in the annular simulation volume, wherein one or more properties of the cement sample can be determined based at least in part on the one or more measurements.

26. The system according to claim 25 further comprising:
an inner fluid-filled chamber within the inner annular surface a pressure of which can be hydraulically controlled to facilitate simulation of radial displacement in the casing.

27. The system according to claim 25 wherein said one or more determined properties are selected from a group consisting of: pore pressure, hydration progress, cement temperature, cement strain, casing strain, crack formation, and micro-annulus formation.

28. The system according to claim 25 wherein said plurality of sensors includes one or more strain gauges positioned on an outer sleeve of metallic material that forms at least part of said outer annular surface, and said one or more determined properties includes cement strain which is based in part on measurements made by said one or more strain gauges.

29. The system according to claim 28 wherein said outer sleeve includes a longitudinal slit which allows said sleeve to expand and contract thereby providing radially displacement of said outer annular surface.

30. A system for simulating a wellbore cementation procedure of a downhole annular region between a casing and a formation wall, the system comprising:
an annular simulation volume configured to receive a cement sample and defined at least in part by an inner annular surface representing an outer surface of the casing and by a water permeable sleeve positioned against an outer annular surface representing an inner surface of the formation wall;
a water delivery system configured to supply water into the annular simulation volume via the water permeable sleeve during hydration of the cement sample placed therein; and
a measurement system including a plurality of sensors configured to make one or more measurements during hydration of the cement sample from which one or more properties of the cement sample can be determined.

* * * * *